(12) United States Patent
Mulier et al.

(10) Patent No.: US 7,470,272 B2
(45) Date of Patent: Dec. 30, 2008

(54) DEVICE AND METHOD FOR ABLATING TISSUE

(75) Inventors: Peter M. J. Mulier, Stillwater, MN (US); Michael F. Hoey, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 369 days.

(21) Appl. No.: 10/882,944

(22) Filed: Jun. 30, 2004

(65) Prior Publication Data

US 2004/0236322 A1 Nov. 25, 2004

Related U.S. Application Data

(60) Continuation of application No. 10/228,006, filed on Aug. 26, 2002, now Pat. No. 6,776,780, which is a continuation of application No. 09/579,916, filed on May 26, 2000, now Pat. No. 6,440,130, which is a division of application No. 09/580,229, filed on May 26, 2000, now Pat. No. 6,443,952, which is a division of application No. 08/901,890, filed on Jul. 29, 1997, now Pat. No. 6,096,037, which is a continuation of application No. 08/896,398, filed on Jul. 18, 1997, now abandoned.

(51) Int. Cl.
*A61B 18/18* (2006.01)

(52) U.S. Cl. ............... 606/51; 606/41; 128/898

(58) Field of Classification Search ............... 606/41, 606/51–52

See application file for complete search history.

(56) References Cited

U.S. PATENT DOCUMENTS

| 1,127,948 | A | 2/1915 | Wappler |
| 2,004,559 | A | 6/1935 | Wappler et al. |
| 3,470,875 | A | 10/1969 | Johnson et al. |
| 3,630,207 | A | 12/1971 | Kahn et al. |
| 3,736,936 | A | 6/1973 | Basiulis et al. |

(Continued)

FOREIGN PATENT DOCUMENTS

DE 43 13 903 9/1994

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Roy D Gibson
(74) *Attorney, Agent, or Firm*—Mike Jaro; Jeffrey J. Hohenshell

(57) ABSTRACT

An electrosurgery medical device is enhanced with unique solution-assistance, and comprises, in combination, co-operating device jaws including jaw portions for manipulating tissue, and a plurality of solution infusion openings defined and spaced along each of the jaw portions, for receiving electrolytic solution and infusing the solution onto and into tissue to be manipulated, along said jaw portions. As preferred, the device further comprises at least one, and most preferably, many, longitudinal groove(s) along at least one and most preferably, both, of the jaw portions, with the solution infusion openings located in the groove or grooves. The solution is energized with RF energy and contributes to the functions and beneficial effects of the instrument. The solution exits the openings in the grooves at sufficient flow rates to separate substantially all the operative surfaces of the device from tissue, thereby substantially completely preventing adherence between the operative surfaces and tissue. The solution is further energized to a range of energy densities such that tissues to be affected are sealed against flow of blood, lymphatic fluids, air, and other bodily fluids and gases.

90 Claims, 9 Drawing Sheets

U.S. PATENT DOCUMENTS

| | | |
|---|---|---|
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,242 A | 8/1975 | Storz |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,043,342 A | 8/1977 | Morrison, Jr. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,312,337 A | 1/1982 | Donohue et al. |
| 4,353,371 A | 10/1982 | Cosman |
| 4,377,168 A | 3/1983 | Rzasa et al. |
| 4,492,231 A | 1/1985 | Auth |
| 4,519,389 A | 5/1985 | Gudkin et al. |
| 4,590,934 A | 5/1986 | Malis et al. |
| 4,598,698 A | 7/1986 | Siegmund |
| 4,601,290 A | 7/1986 | Effron et al. |
| 4,664,110 A | 5/1987 | Schanzlin |
| 4,671,274 A * | 6/1987 | Sorochenko .................. 606/51 |
| 4,706,667 A | 11/1987 | Roos |
| 4,732,149 A | 3/1988 | Sutter |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,940,064 A | 7/1990 | Desai |
| 4,946,460 A | 8/1990 | Merry et al. |
| 4,985,030 A | 1/1991 | Melzer et al. |
| 5,009,661 A | 4/1991 | Michelson |
| 5,013,312 A | 5/1991 | Parins et al. |
| 5,029,574 A | 7/1991 | Shimamura et al. |
| 5,033,477 A | 7/1991 | Chin et al. |
| 5,044,165 A | 9/1991 | Linner et al. |
| 5,044,947 A | 9/1991 | Sachdeva et al. |
| 5,071,428 A | 12/1991 | Chin et al. |
| 5,078,713 A | 1/1992 | Varney |
| 5,080,102 A | 1/1992 | Dory |
| 5,080,660 A | 1/1992 | Buelina |
| 5,083,565 A | 1/1992 | Parins |
| 5,085,657 A | 2/1992 | Ben-Simhon |
| 5,087,243 A | 2/1992 | Avitall |
| 5,100,388 A | 3/1992 | Behl et al. |
| 5,108,390 A | 4/1992 | Potocky et al. |
| 5,116,332 A | 5/1992 | Lottick |
| 5,125,928 A | 6/1992 | Parins et al. |
| 5,147,355 A | 9/1992 | Freidman et al. |
| 5,151,102 A | 9/1992 | Kamiyama et al. |
| 5,156,613 A | 10/1992 | Sawyer |
| 5,167,659 A | 12/1992 | Ohtomo et al. |
| 5,178,133 A | 1/1993 | Pena |
| 5,190,541 A | 3/1993 | Abele et al. |
| 5,207,674 A | 5/1993 | Hamilton |
| 5,207,691 A | 5/1993 | Nardella |
| 5,217,460 A | 6/1993 | Knoepfler |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,242,441 A | 9/1993 | Avitall |
| 5,242,458 A | 9/1993 | Bendel et al. |
| 5,250,047 A | 10/1993 | Rydell |
| 5,250,075 A | 10/1993 | Badie |
| 5,254,116 A | 10/1993 | Baust et al. |
| 5,254,130 A | 10/1993 | Poncet et al. |
| 5,263,493 A | 11/1993 | Avitall |
| 5,269,291 A | 12/1993 | Carter |
| 5,269,326 A | 12/1993 | Verrier |
| 5,269,780 A | 12/1993 | Roos |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,281,216 A | 1/1994 | Klicek |
| 5,293,869 A | 3/1994 | Edwards et al. |
| 5,295,484 A | 3/1994 | Marcus et al. |
| 5,300,087 A | 4/1994 | Knoepfler |
| 5,306,234 A | 4/1994 | Johnson |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,318,589 A | 6/1994 | Lichtman |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,327,905 A | 7/1994 | Avitall |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,354,297 A | 10/1994 | Avitall |
| 5,357,956 A | 10/1994 | Nardella |
| 5,361,752 A | 11/1994 | Moll et al. |
| 5,364,394 A | 11/1994 | Mehl |
| 5,385,148 A | 1/1995 | Lesh et al. |
| 5,391,166 A | 2/1995 | Eggers |
| 5,395,312 A | 3/1995 | Desai |
| 5,396,887 A | 3/1995 | Imran |
| 5,397,304 A | 3/1995 | Truckai |
| 5,397,339 A | 3/1995 | Desai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,403,312 A | 4/1995 | Yates et al. |
| 5,405,376 A | 4/1995 | Mulier et al. |
| 5,409,483 A | 4/1995 | Campbell et al. |
| 5,421,819 A | 6/1995 | Edwards et al. |
| 5,423,807 A | 6/1995 | Milder |
| 5,423,811 A | 6/1995 | Imran et al. |
| 5,427,119 A | 6/1995 | Swartz et al. |
| 5,429,131 A | 7/1995 | Scheinman et al. |
| 5,429,636 A | 7/1995 | Shikhman et al. |
| 5,431,649 A | 7/1995 | Mulier et al. |
| 5,433,708 A | 7/1995 | Nichols et al. |
| 5,435,308 A | 7/1995 | Gallup et al. |
| 5,435,805 A | 7/1995 | Edwards et al. |
| 5,437,651 A | 8/1995 | Todd et al. |
| 5,438,302 A | 8/1995 | Goble |
| 5,441,483 A | 8/1995 | Avitall |

| | | | | | | |
|---|---|---|---|---|---|---|
| 5,443,463 A | 8/1995 | Stern et al. | | 5,591,125 A | 1/1997 | Edwards et al. |
| 5,443,470 A | 8/1995 | Stern et al. | | 5,595,183 A | 1/1997 | Swanson et al. |
| 5,445,638 A * | 8/1995 | Rydell et al. ............... 606/51 | | 5,599,294 A | 2/1997 | Edwards et al. |
| 5,449,355 A | 9/1995 | Rhum et al. | | 5,599,295 A | 2/1997 | Rosen et al. |
| 5,450,843 A | 9/1995 | Moll et al. | | 5,599,350 A | 2/1997 | Schulze et al. |
| 5,451,223 A | 9/1995 | Ben-Simhon | | 5,607,389 A | 3/1997 | Edwards et al. |
| 5,452,582 A | 9/1995 | Longsworth | | 5,607,462 A | 3/1997 | Imran |
| 5,452,733 A | 9/1995 | Sterman et al. | | 5,609,151 A | 3/1997 | Mulier et al. |
| 5,454,370 A | 10/1995 | Avitall | | 5,611,813 A | 3/1997 | Lichtman |
| 5,456,598 A | 10/1995 | McDonough et al. | | 5,617,854 A | 4/1997 | Munsif |
| 5,458,598 A | 10/1995 | Feinberg et al. | | 5,620,459 A | 4/1997 | Lichtman |
| 5,462,545 A | 10/1995 | Wang et al. | | 5,630,794 A | 5/1997 | Lax et al. |
| 5,465,716 A | 11/1995 | Avitall | | 5,630,837 A | 5/1997 | Crowley |
| 5,465,717 A | 11/1995 | Imran et al. | | 5,633,578 A * | 5/1997 | Eggers et al. ............... 323/301 |
| 5,469,853 A | 11/1995 | Law et al. | | 5,637,090 A | 6/1997 | McGee et al. |
| 5,470,308 A | 11/1995 | Edwards et al. | | 5,637,110 A | 6/1997 | Pennybacker et al. |
| 5,470,309 A | 11/1995 | Edwards et al. | | 5,642,736 A | 7/1997 | Avitall |
| 5,472,441 A | 12/1995 | Edwards et al. | | 5,643,197 A | 7/1997 | Brucker et al. |
| 5,472,443 A * | 12/1995 | Cordis et al. ............... 606/48 | | 5,647,871 A | 7/1997 | Levine et al. |
| 5,472,876 A | 12/1995 | Fahy | | 5,655,219 A | 8/1997 | Jusa et al. |
| 5,478,309 A | 12/1995 | Sweezer et al. | | 5,656,029 A | 8/1997 | Imran et al. |
| 5,478,330 A | 12/1995 | Imran et al. | | 5,658,278 A | 8/1997 | Imran et al. |
| 5,480,409 A | 1/1996 | Riza | | 5,667,488 A | 9/1997 | Lundquist et al. |
| 5,484,400 A | 1/1996 | Edwards et al. | | 5,671,747 A | 9/1997 | Connor |
| 5,486,193 A | 1/1996 | Bourne et al. | | 5,672,153 A | 9/1997 | Lax et al. |
| 5,487,385 A | 1/1996 | Avitall | | 5,672,174 A | 9/1997 | Gough et al. |
| 5,487,757 A | 1/1996 | Truckai et al. | | 5,673,695 A | 10/1997 | McGee et al. |
| 5,496,312 A | 3/1996 | Klicek | | 5,674,220 A | 10/1997 | Fox et al. |
| 5,497,774 A | 3/1996 | Swartz et al. | | 5,676,662 A | 10/1997 | Fleischhacker et al. |
| 5,498,248 A | 3/1996 | Milder | | 5,676,692 A | 10/1997 | Sanghvi et al. |
| 5,500,011 A | 3/1996 | Desai | | 5,676,693 A | 10/1997 | Lafontaine |
| 5,500,012 A | 3/1996 | Brucker et al. | | 5,678,550 A | 10/1997 | Bassen et al. |
| 5,505,730 A | 4/1996 | Edwards | | 5,680,860 A | 10/1997 | Imran |
| 5,516,505 A | 5/1996 | McDow | | 5,681,277 A | 10/1997 | Edwards et al. |
| 5,520,682 A | 5/1996 | Baust et al. | | 5,681,278 A | 10/1997 | Igo et al. |
| 5,522,870 A | 6/1996 | Ben-Zion | | 5,681,308 A | 10/1997 | Edwards et al. |
| 5,531,744 A | 7/1996 | Nardella et al. | | 5,683,384 A | 11/1997 | Gough et al. |
| 5,536,267 A | 7/1996 | Edwards et al. | | 5,687,723 A | 11/1997 | Avitall |
| 5,542,915 A | 8/1996 | Edwards et al. | | 5,687,737 A | 11/1997 | Branham et al. |
| 5,545,171 A | 8/1996 | Sharkey et al. | | 5,688,267 A | 11/1997 | Panescu et al. |
| 5,545,195 A | 8/1996 | Lennox et al. | | 5,688,270 A | 11/1997 | Yates et al. |
| 5,545,200 A | 8/1996 | West et al. | | 5,690,611 A | 11/1997 | Swartz et al. |
| 5,549,636 A | 8/1996 | Li | | 5,693,051 A | 12/1997 | Schulze et al. |
| 5,549,661 A | 8/1996 | Kordis et al. | | 5,697,536 A | 12/1997 | Eggers et al. |
| 5,554,110 A | 9/1996 | Edwards et al. | | 5,697,882 A | 12/1997 | Eggers et al. |
| 5,555,883 A | 9/1996 | Avitall | | 5,697,925 A | 12/1997 | Taylor |
| 5,556,377 A | 9/1996 | Rosen et al. | | 5,697,927 A | 12/1997 | Imran et al. |
| 5,558,671 A | 9/1996 | Yates | | 5,697,928 A | 12/1997 | Walcott et al. |
| 5,558,673 A | 9/1996 | Edwards et al. | | 5,702,359 A | 12/1997 | Hofmann et al. |
| 5,560,362 A | 10/1996 | Sliwa, Jr. et al. | | 5,702,390 A | 12/1997 | Austin et al. |
| 5,562,699 A | 10/1996 | Heimberger et al. | | 5,702,438 A | 12/1997 | Avitall |
| 5,562,700 A | 10/1996 | Huitema et al. | | 5,709,680 A | 1/1998 | Yates et al. |
| 5,562,720 A | 10/1996 | Stern et al. | | 5,713,942 A | 2/1998 | Stern |
| 5,562,721 A | 10/1996 | Marchlinski et al. | | 5,716,389 A | 2/1998 | Walinsky et al. |
| 5,564,440 A | 10/1996 | Swartz et al. | | 5,718,241 A | 2/1998 | Ben-Haim et al. |
| 5,569,241 A | 10/1996 | Edwards | | 5,718,701 A | 2/1998 | Shai et al. |
| 5,569,242 A | 10/1996 | Lax et al. | | 5,718,703 A | 2/1998 | Chin |
| 5,569,243 A | 10/1996 | Kortenbach et al. | | 5,720,718 A | 2/1998 | Rosen et al. |
| 5,571,088 A | 11/1996 | Lennox et al. | | 5,720,775 A | 2/1998 | Lanard |
| 5,571,215 A | 11/1996 | Sterman et al. | | 5,722,402 A | 3/1998 | Swanson et al. |
| 5,573,532 A | 11/1996 | Chang et al. | | 5,722,403 A | 3/1998 | McGee et al. |
| 5,575,766 A | 11/1996 | Swartz et al. | | 5,725,512 A | 3/1998 | Swartz et al. |
| 5,575,788 A | 11/1996 | Baker et al. | | 5,725,524 A | 3/1998 | Mulier et al. |
| 5,575,805 A | 11/1996 | Li | | 5,728,143 A | 3/1998 | Gough et al. |
| 5,575,810 A | 11/1996 | Swanson et al. | | 5,730,074 A | 3/1998 | Peter |
| 5,578,007 A | 11/1996 | Imran | | 5,730,127 A | 3/1998 | Avitall |
| 5,582,589 A | 12/1996 | Edwards et al. | | 5,730,704 A | 3/1998 | Avitall |
| 5,582,609 A | 12/1996 | Swanson et al. | | 5,733,280 A | 3/1998 | Avitall |
| 5,584,872 A | 12/1996 | LaFontaine et al. | | 5,735,280 A | 4/1998 | Sherman et al. |
| 5,587,723 A | 12/1996 | Otake et al. | | 5,735,290 A | 4/1998 | Sterman et al. |
| 5,588,432 A | 12/1996 | Crowley | | 5,735,847 A | 4/1998 | Gough et al. |
| 5,588,960 A | 12/1996 | Edwards et al. | | 5,735,849 A * | 4/1998 | Baden et al. ............... 606/51 |
| 5,590,657 A | 1/1997 | Cain et al. | | 5,740,808 A | 4/1998 | Panescu et al. |

| | | | | | |
|---|---|---|---|---|---|
| 5,743,906 A * | 4/1998 | Parins et al. .......... 606/51 | 5,891,138 A | 4/1999 | Tu et al. |
| 5,749,846 A | 5/1998 | Edwards et al. | 5,891,142 A * | 4/1999 | Eggers et al. .......... 606/51 |
| 5,755,664 A | 5/1998 | Rubenstein | 5,893,848 A | 4/1999 | Negus et al. |
| 5,755,717 A | 5/1998 | Yates et al. | 5,893,863 A | 4/1999 | Yoon |
| 5,755,760 A | 5/1998 | Maguire et al. | 5,895,417 A | 4/1999 | Pomeranz et al. |
| 5,759,158 A | 6/1998 | Swanson | 5,897,553 A | 4/1999 | Mulier |
| 5,769,846 A | 6/1998 | Edwards et al. | 5,897,554 A | 4/1999 | Chia et al. |
| 5,776,128 A | 7/1998 | Eggers | 5,899,898 A | 5/1999 | Arless et al. |
| 5,776,130 A | 7/1998 | Buysse et al. | 5,899,899 A | 5/1999 | Arless et al. |
| 5,782,827 A | 7/1998 | Gough et al. | 5,902,289 A | 5/1999 | Swartz et al. |
| 5,782,828 A | 7/1998 | Chen et al. | 5,904,711 A | 5/1999 | Flom et al. |
| 5,785,706 A | 7/1998 | Bednarek | 5,906,580 A | 5/1999 | Kline-Schoder et al. |
| H1745 H | 8/1998 | Paraschac | 5,906,587 A | 5/1999 | Zimmon |
| 5,788,636 A | 8/1998 | Curley | 5,906,606 A | 5/1999 | Chee et al. |
| 5,792,140 A | 8/1998 | Tu et al. | 5,908,029 A | 6/1999 | Knudson et al. |
| 5,797,906 A | 8/1998 | Rhum et al. | 5,910,129 A | 6/1999 | Koblish et al. |
| 5,797,960 A | 8/1998 | Stevens et al. | 5,913,855 A | 6/1999 | Gough et al. |
| 5,800,428 A | 9/1998 | Nelson et al. | 5,916,213 A | 6/1999 | Haissaguerre et al. |
| 5,800,482 A | 9/1998 | Pomeranz et al. | 5,916,214 A | 6/1999 | Cosio et al. |
| 5,800,484 A | 9/1998 | Gough et al. | 5,921,924 A | 7/1999 | Avitall |
| 5,807,393 A | 9/1998 | Williamson et al. | 5,921,982 A | 7/1999 | Lesh et al. |
| 5,807,395 A | 9/1998 | Mulier et al. | 5,924,424 A | 7/1999 | Stevens et al. |
| 5,810,802 A | 9/1998 | Panescu et al. | 5,925,038 A | 7/1999 | Panescu et al. |
| 5,810,804 A | 9/1998 | Gough et al. | 5,925,042 A | 7/1999 | Gough et al. |
| 5,810,805 A | 9/1998 | Sutcu et al. | 5,927,284 A | 7/1999 | Borst et al. |
| 5,810,811 A | 9/1998 | Yates et al. | 5,928,191 A | 7/1999 | Houser et al. |
| 5,814,028 A | 9/1998 | Swartz et al. | 5,928,229 A | 7/1999 | Gough et al. |
| 5,817,091 A | 10/1998 | Nardella et al. | 5,931,810 A | 8/1999 | Grabek |
| 5,817,093 A | 10/1998 | Williamson, IV et al. | 5,931,836 A | 8/1999 | Hatta et al. |
| 5,823,955 A | 10/1998 | Kuck et al. | 5,931,848 A | 8/1999 | Saadat |
| 5,823,956 A | 10/1998 | Roth et al. | 5,935,126 A | 8/1999 | Riza |
| 5,827,216 A | 10/1998 | Igo et al. | 5,938,660 A | 8/1999 | Swartz et al. |
| 5,827,271 A | 10/1998 | Buysse et al. | 5,941,251 A | 8/1999 | Panescu et al. |
| 5,829,447 A | 11/1998 | Stevens et al. | 5,941,845 A | 8/1999 | Tu et al. |
| 5,833,690 A | 11/1998 | Yates et al. | 5,944,718 A | 8/1999 | Austin et al. |
| 5,833,703 A | 11/1998 | Manushakian | 5,947,938 A | 9/1999 | Swartz et al. |
| 5,836,947 A | 11/1998 | Fleischman et al. | 5,951,547 A | 9/1999 | Gough et al. |
| 5,840,030 A | 11/1998 | Ferek-Petric et al. | 5,951,552 A | 9/1999 | Long et al. |
| 5,842,984 A | 12/1998 | Avitall | 5,954,661 A | 9/1999 | Greenspon et al. |
| 5,843,075 A | 12/1998 | Taylor | 5,954,665 A | 9/1999 | Ben-Haim |
| 5,843,122 A | 12/1998 | Riza | 5,957,922 A | 9/1999 | Imran |
| 5,844,349 A | 12/1998 | Oakley et al. | 5,961,514 A | 10/1999 | Long et al. |
| 5,846,187 A | 12/1998 | Wells et al. | 5,964,727 A | 10/1999 | Edwards et al. |
| 5,846,191 A | 12/1998 | Wells et al. | 5,964,755 A | 10/1999 | Edwards |
| 5,846,238 A | 12/1998 | Jackson et al. | 5,967,976 A | 10/1999 | Larsen |
| 5,849,011 A | 12/1998 | Jones et al. | 5,971,980 A | 10/1999 | Sherman |
| 5,849,020 A | 12/1998 | Long et al. | 5,971,983 A | 10/1999 | Lesh |
| 5,849,028 A | 12/1998 | Chen | 5,972,026 A | 10/1999 | Laufer et al. |
| 5,853,411 A | 12/1998 | Whayne et al. | 5,980,516 A | 11/1999 | Mulier et al. |
| 5,855,590 A | 1/1999 | Malecki et al. | 5,980,517 A | 11/1999 | Gough |
| 5,855,614 A | 1/1999 | Stevens et al. | 5,984,281 A | 11/1999 | Hacker et al. |
| 5,860,975 A | 1/1999 | Goble et al. | 5,993,447 A | 11/1999 | Blewett et al. |
| 5,863,290 A | 1/1999 | Gough et al. | 5,997,533 A | 12/1999 | Kuhns |
| 5,863,291 A | 1/1999 | Schaer | 6,007,499 A | 12/1999 | Martin et al. |
| 5,868,737 A | 2/1999 | Taylor et al. | 6,010,516 A | 1/2000 | Hulka |
| 5,871,481 A | 2/1999 | Kannenberg et al. | 6,010,531 A | 1/2000 | Donlon et al. |
| 5,871,483 A | 2/1999 | Jackson et al. | 6,012,457 A | 1/2000 | Lesh |
| 5,871,523 A | 2/1999 | Fleischman et al. | 6,013,074 A | 1/2000 | Taylor |
| 5,871,525 A | 2/1999 | Edwards et al. | 6,016,809 A | 1/2000 | Mulier et al. |
| 5,873,845 A | 2/1999 | Cline et al. | 6,016,811 A | 1/2000 | Knopp et al. |
| 5,873,877 A | 2/1999 | McGaffigan et al. | 6,017,358 A | 1/2000 | Yoon et al. |
| 5,873,896 A | 2/1999 | Ideker | 6,022,334 A | 2/2000 | Edwards et al. |
| 5,876,398 A | 3/1999 | Mulier et al. | 6,023,638 A | 2/2000 | Swanson |
| 5,876,399 A | 3/1999 | Chia et al. | 6,024,740 A | 2/2000 | Lesh et al. |
| 5,876,400 A | 3/1999 | Songer | 6,024,741 A | 2/2000 | Williamson et al. |
| 5,876,401 A | 3/1999 | Schulze et al. | 6,030,403 A | 2/2000 | Long et al. |
| 5,879,295 A | 3/1999 | Li et al. | 6,033,402 A | 3/2000 | Tu et al. |
| 5,879,296 A | 3/1999 | Ockuly et al. | 6,036,670 A | 3/2000 | Wijeratne et al. |
| 5,881,732 A | 3/1999 | Sung et al. | 6,039,731 A | 3/2000 | Taylor et al. |
| 5,882,346 A | 3/1999 | Pomeranz et al. | 6,039,733 A | 3/2000 | Buysse et al. |
| 5,885,278 A | 3/1999 | Fleischman | 6,039,748 A | 3/2000 | Savage et al. |
| 5,891,135 A | 4/1999 | Jackson et al. | 6,042,556 A | 3/2000 | Beach et al. |
| 5,891,136 A | 4/1999 | McGee et al. | 6,047,218 A | 4/2000 | Whayne et al. |

| | | | |
|---|---|---|---|
| 6,048,329 A | 4/2000 | Thompson et al. | |
| 6,050,996 A | 4/2000 | Schmaltz et al. | |
| 6,063,081 A | 5/2000 | Mulier | |
| 6,064,902 A | 5/2000 | Haissaguerre et al. | |
| 6,068,653 A | 5/2000 | LaFontaine | |
| 6,071,279 A | 6/2000 | Whayne et al. | |
| 6,071,281 A | 6/2000 | Burnside et al. | |
| 6,083,150 A | 7/2000 | Aznoian et al. | |
| 6,083,222 A | 7/2000 | Klein et al. | |
| 6,088,894 A | 7/2000 | Oakley | |
| 6,096,037 A | 8/2000 | Mulier | |
| 6,102,886 A | 8/2000 | Lundquist et al. | |
| 6,110,098 A | 8/2000 | Renirie et al. | |
| 6,113,592 A | 9/2000 | Taylor | |
| 6,113,595 A | 9/2000 | Muntermann | |
| 6,113,598 A | 9/2000 | Baker | |
| 6,117,101 A | 9/2000 | Diederich et al. | |
| 6,120,496 A | 9/2000 | Whayne et al. | |
| 6,123,703 A | 9/2000 | Tu et al. | |
| H1904 H | 10/2000 | Yates et al. | |
| 6,126,658 A | 10/2000 | Baker | |
| 6,129,726 A | 10/2000 | Edwards et al. | |
| 6,142,993 A | 11/2000 | Whayne et al. | |
| 6,142,994 A | 11/2000 | Swanson et al. | |
| 6,152,920 A | 11/2000 | Thompson et al. | |
| 6,156,033 A | 12/2000 | Tu et al. | |
| 6,161,543 A | 12/2000 | Cox et al. | |
| 6,162,220 A | 12/2000 | Nezhat | |
| 6,165,174 A | 12/2000 | Jacobs et al. | |
| 6,179,837 B1 | 1/2001 | Hooven | |
| 6,193,713 B1 | 2/2001 | Geistert et al. | |
| 6,193,714 B1 | 2/2001 | McGaffigan et al. | |
| 6,206,847 B1 | 3/2001 | Edwards et al. | |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,264,087 B1 | 7/2001 | Whitman | |
| 6,267,761 B1 | 7/2001 | Ryan | |
| 6,270,471 B1 | 8/2001 | Hechel et al. | |
| 6,273,887 B1 | 8/2001 | Yamauchi et al. | |
| 6,277,117 B1 | 8/2001 | Tetzlaff et al. | |
| 6,292,678 B1 | 9/2001 | Hall et al. | |
| 6,293,943 B1 | 9/2001 | Panescu et al. | |
| 6,296,619 B1 | 10/2001 | Brisken et al. | |
| 6,296,640 B1 | 10/2001 | Wampler et al. | |
| 6,302,880 B1 | 10/2001 | Schaer | |
| 6,302,903 B1 | 10/2001 | Mulier et al. | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,325,797 B1 | 12/2001 | Stewart et al. | |
| 6,328,736 B1 | 12/2001 | Mulier | |
| 6,332,089 B1 | 12/2001 | Acker et al. | |
| 6,332,881 B1 | 12/2001 | Carner et al. | |
| 6,334,860 B1 | 1/2002 | Dorn | |
| 6,356,790 B1 | 3/2002 | Maguire et al. | |
| 6,358,248 B1 | 3/2002 | Mulier | |
| 6,358,249 B1 | 3/2002 | Chen et al. | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,391,024 B1 | 5/2002 | Sun et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,419,653 B2 | 7/2002 | Edwards et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier | |
| 6,443,970 B1 | 9/2002 | Schulze et al. | |
| 6,447,507 B1 | 9/2002 | Bednarek et al. | |
| 6,451,013 B1 | 9/2002 | Bays et al. | |
| 6,461,314 B1 | 10/2002 | Pant et al. | |
| 6,461,956 B1 | 10/2002 | Patterson | |
| 6,464,661 B2 | 10/2002 | Edwards et al. | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,484,727 B1 | 11/2002 | Vaska et al. | |
| 6,488,678 B2 | 12/2002 | Sherman | |
| 6,488,680 B1 | 12/2002 | Francischelli | |
| 6,497,705 B2 | 12/2002 | Comben | |
| 6,502,575 B1 | 1/2003 | Jacobs et al. | |
| 6,506,189 B1 | 1/2003 | Rittman, III et al. | |
| 6,514,250 B1 | 2/2003 | Jahns | |
| 6,517,536 B2 | 2/2003 | Hooven et al. | |
| 6,527,767 B2 | 3/2003 | Wang et al. | |
| 6,527,769 B2 | 3/2003 | Langberg et al. | |
| 6,537,248 B2 | 3/2003 | Mulier | |
| 6,537,272 B2 | 3/2003 | Christopherson et al. | |
| 6,540,740 B2 | 4/2003 | Lehmann et al. | |
| 6,546,935 B2 | 4/2003 | Hooven | |
| 6,547,785 B1 | 4/2003 | Heiner et al. | |
| 6,551,300 B1 | 4/2003 | McGaffigan | |
| 6,558,382 B2 | 5/2003 | Jahns | |
| 6,575,968 B1 | 6/2003 | Eggers et al. | |
| 6,575,969 B1 | 6/2003 | Rittman, III et al. | |
| 6,584,360 B2 | 6/2003 | Francischelli | |
| 6,585,732 B2 | 7/2003 | Mulier | |
| 6,595,934 B1 | 7/2003 | Hissong et al. | |
| 6,602,247 B2 | 8/2003 | Lalonde | |
| 6,605,084 B2 | 8/2003 | Acker et al. | |
| 6,607,529 B1 | 8/2003 | Jones et al. | |
| 6,610,054 B1 | 8/2003 | Edwards et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,623,515 B2 | 9/2003 | Mulier et al. | |
| 6,632,222 B1 | 10/2003 | Edwards et al. | |
| 6,645,199 B1 | 11/2003 | Jenkins et al. | |
| 6,648,883 B2 | 11/2003 | Francischelli | |
| 6,652,518 B2 | 11/2003 | Wellman et al. | |
| 6,656,175 B2 | 12/2003 | Francischelli | |
| 6,663,627 B2 | 12/2003 | Francischelli | |
| 6,672,312 B2 | 1/2004 | Acker | |
| 6,679,882 B1 | 1/2004 | Kornerup | |
| 6,692,450 B1 | 2/2004 | Coleman | |
| 6,692,491 B1 | 2/2004 | Phan | |
| 6,692,492 B2 | 2/2004 | Simpson et al. | |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,723,092 B2 | 4/2004 | Brown et al. | |
| 6,730,079 B2 | 5/2004 | Lovewell | |

| Patent Number | Date | Name |
|---|---|---|
| 6,736,810 B2 | 5/2004 | Hoey |
| 6,740,080 B2 | 5/2004 | Jain et al. |
| 6,752,806 B2 | 6/2004 | Durgin et al. |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,814,712 B1 | 11/2004 | Edwards et al. |
| 6,817,999 B2 | 11/2004 | Berube et al. |
| 6,827,715 B2 | 12/2004 | Francischelli |
| 6,849,073 B2 | 2/2005 | Hoey |
| 6,849,075 B2 | 2/2005 | Bertolero et al. |
| 6,852,091 B2 | 2/2005 | Edwards et al. |
| 6,855,141 B2 | 2/2005 | Lovewell |
| 6,858,028 B2 | 2/2005 | Mulier |
| 6,887,238 B2 | 5/2005 | Jahns |
| 6,889,694 B2 | 5/2005 | Hooven |
| 6,896,673 B2 | 5/2005 | Hooven |
| 6,899,709 B2 | 5/2005 | Lehmann et al. |
| 6,899,710 B2 | 5/2005 | Hooven |
| 6,899,711 B2 | 5/2005 | Stewart et al. |
| 6,905,498 B2 | 6/2005 | Hooven |
| 6,911,019 B2 | 6/2005 | Mulier |
| 6,916,318 B2 | 7/2005 | Francischelli |
| 6,923,806 B2 | 8/2005 | Hooven |
| 6,929,010 B2 | 8/2005 | Vaska et al. |
| 6,932,811 B2 | 8/2005 | Hooven |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 6,964,660 B2 | 11/2005 | Maguire et al. |
| 6,974,454 B2 | 12/2005 | Hooven |
| 6,989,010 B2 | 1/2006 | Francischelli et al. |
| 7,001,415 B2 | 2/2006 | Hooven |
| 7,004,938 B2 | 2/2006 | Ormsby et al. |
| 7,029,470 B2 | 4/2006 | Francischelli et al. |
| 7,083,620 B2 | 8/2006 | Jahns et al. |
| 7,094,235 B2 | 8/2006 | Francischelli |
| 7,118,566 B2 | 10/2006 | Jahns |
| 7,128,740 B2 | 10/2006 | Jacobs et al. |
| 7,147,633 B2 | 12/2006 | Chee et al. |
| 7,156,845 B2 | 1/2007 | Mulier et al. |
| 7,166,105 B2 | 1/2007 | Mulier et al. |
| 7,169,144 B2 | 1/2007 | Hoey et al. |
| 7,201,731 B1 | 4/2007 | Lundquist et al. |
| 7,241,292 B2 | 7/2007 | Hooven |
| 7,247,155 B2 | 7/2007 | Hoey et al. |
| 7,250,048 B2 | 7/2007 | Francischelli et al. |
| 7,250,051 B2 | 7/2007 | Francischelli |
| 7,261,711 B2 | 8/2007 | Mulier et al. |
| 7,276,061 B2 | 10/2007 | Schaer et al. |
| 7,294,143 B2 | 11/2007 | Francischelli |
| 2001/0039419 A1 | 11/2001 | Francischelli et al. |
| 2002/0019629 A1 | 2/2002 | Dietz et al. |
| 2002/0052602 A1 | 5/2002 | Wang et al. |
| 2002/0107513 A1 | 8/2002 | Hooven |
| 2002/0107514 A1 | 8/2002 | Hooven |
| 2003/0009094 A1 | 1/2003 | Segner et al. |
| 2003/0028187 A1 | 2/2003 | Vaska et al. |
| 2003/0045872 A1 | 3/2003 | Jacobs |
| 2003/0050557 A1 | 3/2003 | Susil et al. |
| 2003/0078575 A1 | 4/2003 | Jahns et al. |
| 2003/0093104 A1 | 5/2003 | Bonner et al. |
| 2003/0130598 A1 | 7/2003 | Manning et al. |
| 2003/0135207 A1 | 7/2003 | Langberg et al. |
| 2003/0144656 A1 | 7/2003 | Ocel |
| 2003/0144657 A1 | 7/2003 | Bowe et al. |
| 2003/0158548 A1 | 8/2003 | Phan et al. |
| 2003/0178032 A1 | 9/2003 | Ingle et al. |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0010203 A1 | 1/2005 | Edwards et al. |
| 2005/0033280 A1 | 2/2005 | Francischelli |
| 2005/0084804 A1 | 4/2005 | Truskett et al. |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0222562 A1 | 10/2005 | Lovewell |
| 2005/0267454 A1 | 12/2005 | Hissong |
| 2006/0009756 A1 | 1/2006 | Francischelli |
| 2006/0009759 A1 | 1/2006 | Christian |
| 2006/0015037 A1 | 1/2006 | Mulier et al. |
| 2006/0020263 A1 | 1/2006 | Rothstein et al. |
| 2006/0020271 A1 | 1/2006 | Stewart et al. |
| 2006/0025756 A1 | 2/2006 | Francischelli et al. |
| 2006/0036236 A1 | 2/2006 | Rothstein et al. |
| 2006/0041243 A1 | 2/2006 | Nayak et al. |
| 2006/0041254 A1 | 2/2006 | Francischelli et al. |
| 2006/0047278 A1 | 3/2006 | Christian et al. |
| 2006/0052770 A1 | 3/2006 | Mulier et al. |
| 2006/0079888 A1 | 4/2006 | Mulier et al. |
| 2006/0084967 A1 | 4/2006 | Jacobs et al. |
| 2006/0142753 A1 | 6/2006 | Francischelli et al. |
| 2006/0195083 A1 | 8/2006 | Jahns et al. |
| 2006/0229594 A1 | 10/2006 | Francischelli et al. |
| 2007/0032786 A1 | 2/2007 | Francischelli |
| 2007/0043397 A1 | 2/2007 | Ocel et al. |
| 2007/0049863 A1 | 3/2007 | Jahns et al. |
| 2007/0093808 A1 | 4/2007 | Mulier et al. |
| 2007/0118107 A1 | 5/2007 | Francischelli et al. |
| 2007/0118114 A1 | 5/2007 | Mulier et al. |
| 2007/0208332 A1 | 9/2007 | Mulier et al. |
| 2007/0270795 A1 | 11/2007 | Francischelli et al. |
| 2007/0270799 A1 | 11/2007 | Francischelli |
| 2007/0270800 A1 | 11/2007 | Francischelli |
| 2008/0015563 A1 | 1/2008 | Hoey et al. |
| 2008/0039746 A1 | 2/2008 | Hissong et al. |
| 2008/0071271 A1 | 3/2008 | Francischelli |

FOREIGN PATENT DOCUMENTS

| | | |
|---|---|---|
| EP | 0 450 608 | 10/1991 |
| EP | 0 765 639 | 4/1997 |
| WO | WO 92/05828 | 4/1992 |
| WO | WO 93/25267 | 12/1993 |
| WO | WO 95/31144 | 11/1995 |
| WO | WO 97/05829 | 2/1997 |
| WO | WO 97/10764 | 3/1997 |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/03414 | 1/1999 |
| WO | WO 99/04696 | 2/1999 |
| WO | WO 99/12487 | 3/1999 |

| | | |
|---|---|---|
| WO | WO 99/44519 | 9/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 | 11/2001 |
| WO | WO 01/82813 | 11/2001 |
| WO | WO 02/087454 | 11/2002 |

OTHER PUBLICATIONS

Gallagher et al., "Cryosurgical Ablation of Accessory Atrioventrical Connections: A Method of Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiolgy 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; Pace, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Tsui et al., "Maze 3 for Atrial Fibrillation: Two Cuts Too Few?" Pace 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," Pace, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Suppl 1):I-493,#2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation,1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983, 198:2;119-129.

Williams, et al., "Left atrial isolation," J Thorac Cardiovas Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Simple Left Atrial Procedure for Chronic Atrial Fibrillation Associated with Mitral Valve Disease," Ann Thorac Surg, 1996;62:1796-1800.

Sueda et al., "Efficacy of a Simple Left Atrial Procedure for Chronic Atrial Fibrillation in Mitral Valve Operations," Ann Thorac Surg, 1997;63:1070-1075.

U.S. Appl. No. 11/881,422, filed Jul. 27, 2007, Francischelli.
U.S. Appl. No. 11/881,442, filed Jul. 27, 2007, Francischelli et al.
U.S. Appl. No. 11/881,443, filed Jul. 27, 2007, Francischelli.
U.S. Appl. No. 11/881,558, filed Jul. 27, 2007, Francischelli.

* cited by examiner

DEVICE AND METHOD FOR ABLATING TISSUE

CROSS REFERENCE TO RELATED APPLICATIONS

This application is a continuation of U.S. Ser. No. 10/228,006, filed Aug. 26, 2002, now U.S. Pat. No. 6,776,780, which is a continuation of U.S. Ser. No. 09/579,916, filed May 26, 2000, now U.S Pat. No. 6,440,130, which is a divisional of U.S. Ser. No. 09/580,229, filed May 26, 2000, now U.S. Pat. No. 6,443,952, which is a divisional of U.S. Ser. No. 08/901,890, filed Jul. 29, 1997, now U.S. Pat. No. 6,096,037, which is a continuation of U.S. Ser. No. 08/896,398, filed Jul. 18, 1997, now abandoned.

BACKGROUND OF THE INVENTION

This invention relates to medical instruments, and more particularly to electrosurgical devices, and methods of manipulating tissue as, for example, by cutting the tissue.

DESCRIPTION OF THE RELATED ART

High-frequency alternating current was used to cut and coagulate human tissue as early as 1911. Current generators and electrode tipped instruments then progressed such that electrosurgical instruments and current generators are available in a multitude of configurations for both open procedures and endoscopic procedures, with microprocessor-controlled currents typically on the order of 500 KHz. Radiofrequency (RF) catheter ablation of brain lesions began in the 1960s, and RF ablation of heart tissue to control supraventricular tachyarrhythmias began in the 1980s. Thus, electrical energy, including but not limited to RF energy, is a known tool for a variety of effects on human tissue, including cutting, coagulating, and ablative necrosis, with and as a part of electrically conductive forceps. Bipolar and monopolar currents are both used with electrosurgical forceps. With monopolar current, a grounding pad is placed under the patient. A recent example of an electrically energized electrosurgical device is disclosed in U.S. Pat. No. 5,403,312 issued on Apr. 4, 1995 to Yates et al., and the disclosure is incorporated by reference.

SUMMARY OF THE INVENTION

An object of the present invention is to provide an electrosurgery tissue sealing medical device which may and also may not be a forceps.

Another object of the present invention is to provide an electrosurgery tissue sealing device such as a forceps that seals tissue by a unique flow of an electrolytic fluid or solution to the manipulating portions of the device in combination with energization of the solution with electrical energy. The effect of the solution and energy may be enhanced with pressure. The solution is brought into contact with and infuses the tissue. The solution may include saline as well as other non-toxic and toxic electrolytic solutions, and may be energized with RF electrical energy. The body of the device itself may or not be energized.

The solution provides at least in part the beneficial functions and effects of the instrument. As preferred, pressure on the tissue is applied, and most preferably the effect of pressure is optimized, as by applying pressure across the tissue to be effected that is substantially uniform.

Another object of the invention is to provide an electrosurgery medical device as described, and methods of sealing tissue, in which tissues are sealed against flow of fluids including air. With the invention, for example, lung tissue is aerostatically and hemostatically sealed, with the tissue adjacent the sealed tissue retaining blood and air.

Another object of the invention is to provide an electrosurgery medical device that may take the form of open surgery forceps of a variety of specific forms, or endoscopic forceps, also of a variety of forms.

A further object of the invention is to provide an electrosurgery medical device as described, in which the electrolytic solution by which the instrument functions is infused from the device onto and/or into the tissue along the operative portions of the device. With and without applied pressure, the solution coagulates and additionally seals tissue, as a result of being energized by RF energy, and also envelopes the operative portions of the device in solution all during manipulation of tissue, substantially completely preventing adherence between the instrument and tissue, substantially without flushing action.

In a principal aspect, then, the invention takes the form of an enhanced solution-assisted electrosurgery medical device comprising, in combination, co-operating device jaws including jaw portions for manipulating tissue, and a plurality of solution infusion openings defined and spaced along each of the jaw portions, for receiving solution and infusing solution onto and into the tissue along said jaw portions. While the device is contemplated with and without grooves, as preferred, the device further comprises at least one, and most preferably, many, longitudinal grooves along at least one and most preferably, both, of the jaw portions. Also most preferably, the solution infusion openings are located on the inside faces of the jaw portions, adjacent to and most preferably in the groove or grooves. The solution exiting the openings separates substantially all the operative surfaces of the device from tissue, substantially completely preventing adherence between the operative surfaces and tissue. The solution also aids in coagulation.

Coagulation aside, the invention causes hemostasis, aerostasis, and more generally, "omnistasis" of substantially any and all liquids and gases found in tissue being treated, such as lymphatic fluids and methane, as well as blood and air. These broader effects are understood to result from such actions as shrinkage of vascalature with and without coagulation, and without desiccation and carbonization.

Also as preferred, the operative portions of the device may take the form of a circular, semicircular or other regular and irregular geometric shape, to contain and/or isolate tissue to be affected and perhaps resected. As an example, with an enclosed geometric shape such as a circle, tissue surrounding lesions and/or tumors of the lung may be aerostatically and hemostatically sealed, resulting in an isolation of the lesions and/or tumors for resection. Lung function is retained. For adaption to unique tissue geometries, the operative portions of the device may be malleable, to be manipulated to substantially any needed contour. For procedures including resection, the device may include an advanceable and retractable blade, or additional functional structures and features.

These and other objects, advantages and features of the invention will become more apparent upon a reading of the detailed description of preferred embodiments of the invention, which follows, and reference to the drawing which accompanies this description.

BRIEF DESCRIPTION OF THE DRAWING

The accompanying drawing includes a variety of figures. Like numbers refer to like parts throughout the drawing. In the drawing.

DESCRIPTION OF THE PREFERRED EMBODIMENTS

Figure 1:
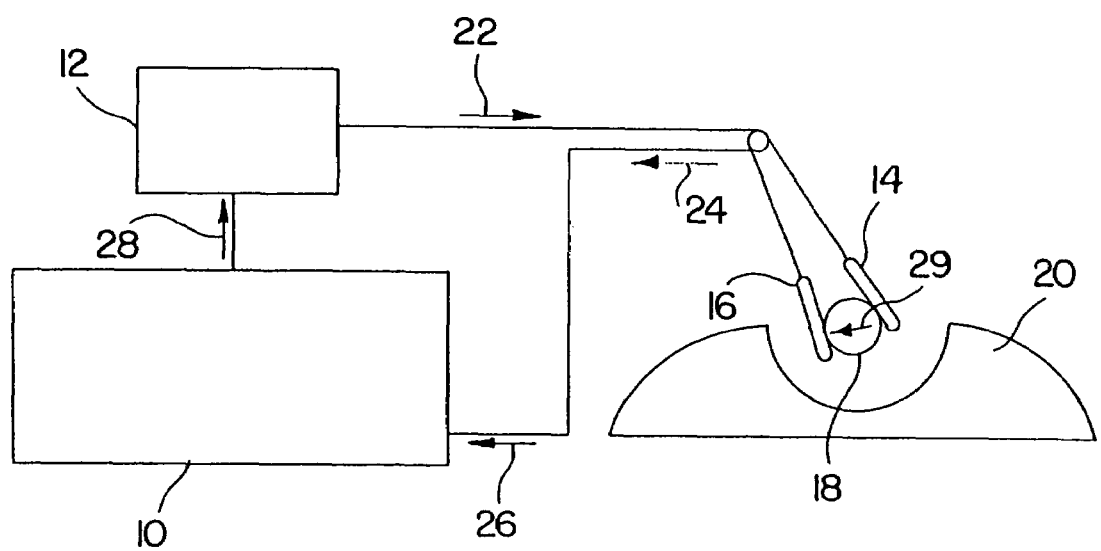
FIG. 1 is a schematic diagram of the key elements of an electrical circuit according to the invention.

Electrosurgery uses electrical energy to heat tissue and cause a variety of effects such as cutting, coagulation and ablative necrosis. The heat arises as the energy dissipates in the resistance of the tissue. The effect is dependent on both temperature and time. Lower temperatures for longer times often yield the same effect as higher temperatures for shorter times. Normal body temperature is approximately 37° C. No significant long-term effect is caused by temperatures in the range of 37° C. to 40° C. In the range of 41° C. to 44° C., cell damage is reversible for exposure times less than several hours. In the range of 45° C. to 49° C., cell damage becomes irreversible at increasingly short intervals. The following table states expected effects at higher temperatures:

| Temperature (° C.) | Effect |
|---|---|
| 50-69 | Irreversible cell damage - ablation necrosis. |
| 70 | Threshold temperature for shrinkage of tissue. (Some collagen hydrogen bonds break at 60-68; those with cross-linkages break at 75-80.) |
| 70-99 | Range of coagulation. Hemostasis due to shrinkage of blood vessels. |
| 100 | Water boils. |
| 100-200 | Desiccation as fluid is vaporized. Dependent on the length of time during which heat is applied, carbonization may occur, and at higher temperatures, occurs quickly. |

This table is not intended as a statement of scientifically precise ranges above and below which no similar effects will be found, and instead, is intended as a statement of generally accepted values which provide approximations of the ranges of the stated effects. Limitation of the appended claims in accordance with this and the further details of this description is intended to the extent such details are incorporated in the claims, and not otherwise.

As a consequence of the foregoing effects, preferred "soft" coagulation occurs at temperatures slightly above 70° C. Heat denatures and shrinks tissues and blood vessels, thereby leading, as desired, to control of bleeding. Cells are generally not ruptured. "Soft" coagulation is generally assured with voltages below 200 peak Volts. Sparks are avoided. "Forced" coagulation can be accomplished with bursts of electrical energy. Electric arcs are generated. Deeper coagulation is achieved, at the cost of some carbonization and an occasional cutting effect. Spray coagulation is also possible. Tissue cutting occurs by desiccation, when the concentration of electrical energy, also referred to here as energy density, is acute, and the temperature of tissue is raised above 100° C.

For both coagulation and cutting by electrical energy, a sine wave waveform is employed, with a frequency of about 500 kHz. For cutting, increasing voltage to as much as 600 peak Volts leads to higher spark intensity which results in deeper cuts. Frequencies above 300,000 Hz avoid stimulating nerve and muscle cells, and generally assure that the effect on tissue is substantially purely thermal.

In contrast with the RF energy tissue-cutting electrosurgery tools of the past, significant purposes of the present invention are to provide a mechanism of avoiding desiccation of tissue at the electrode/tissue interface and to achieve sealing of tissues. By "sealing," the effects of hemostasis, or arresting of bleeding; "aerostasis," or arresting of the passage of air; and closure of tissues such as blood vessels against larger-scale passage of blood, among other effects, are intended. More specifically, the effect of sealing at the cellular level is a primary focus, as is sealing at the vascular level.

Referring to FIG. 1, key elements of a preferred electrical circuit according to the invention include an electrosurgical unit 10, a switch 12, and electrodes 14, 16. An effect is created on tissue 18 of a body 20. One electrode such as electrode 14 acts as a positive or active electrode, while the other such as electrode 16 acts as a negative or return electrode. Current flows directly from one electrode to the other primarily through only the tissue, as shown by arrows 22, 24, 26, 28, 29. No pad is needed under the patient. This is a bipolar configuration.

Figure 2:
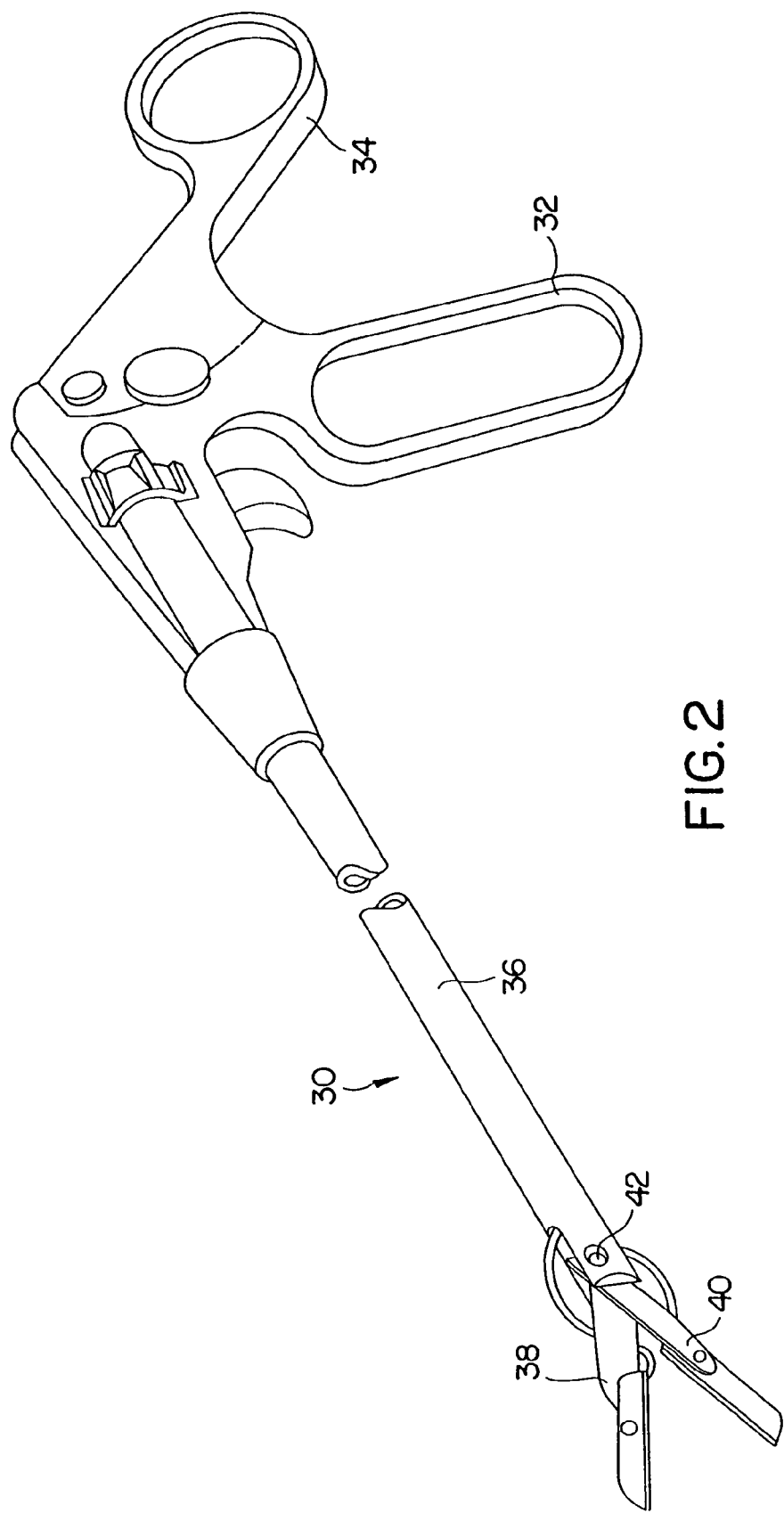
FIG. 2 is a perspective view of an endoscopic forceps according to the invention.
Figure 3:
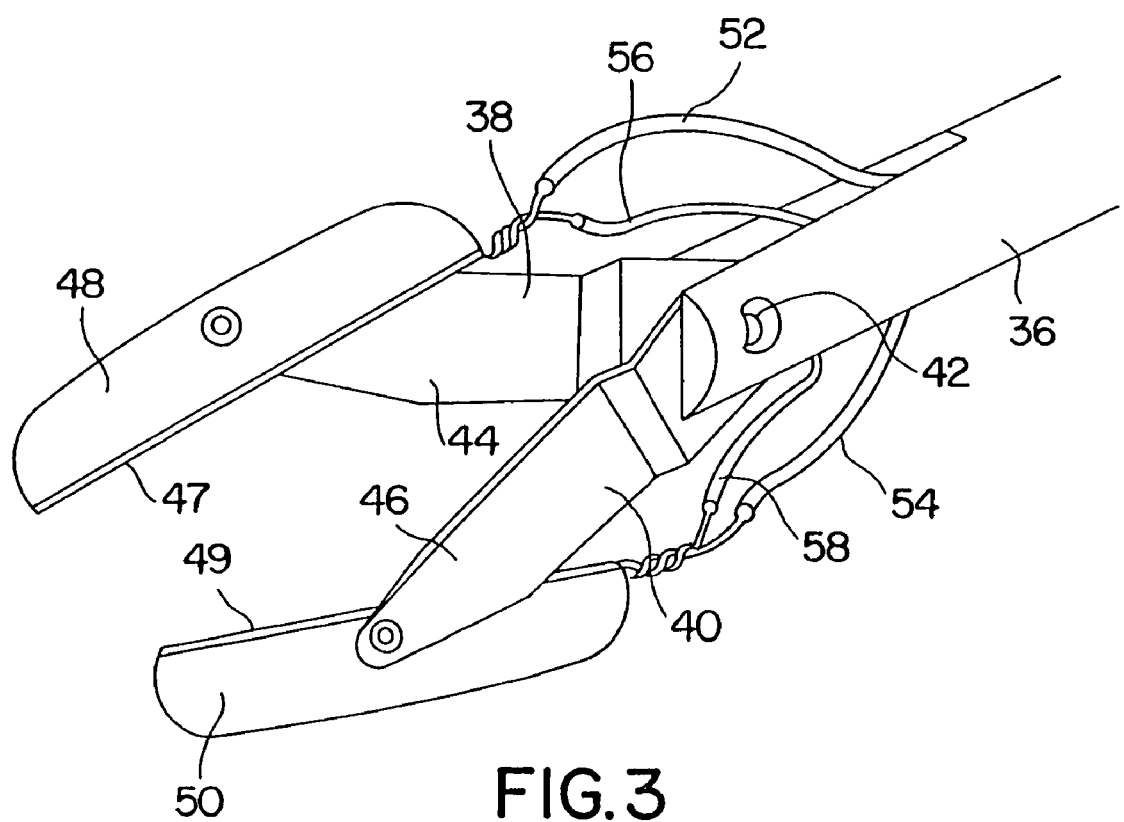
FIG. 3 is a detail view of a portion of the forceps of FIG. 2.

Referring to FIG. 2, a forceps 30 according to the invention is an endoscopic forceps, and includes manual handles 32, 34, an elongated shaft 36, and jaws 38, 40. The handles 32, 34 pivot together and apart and through a suitable mechanism (not shown; present in the incorporated prior art) control the jaws 38, 40 to also pivot together and apart about a pivot connection 42. Referring to FIG. 3, each jaw 38, 40 is formed in two parts, hinged together. The jaw 38 includes a link portion 44 connected directly to the forceps shaft 36, and the jaw 40 includes a link portion 46 also connected directly to the forceps shaft 36. A jaw portion 48 hingedly fastened to the jaw link portion 44 completes the jaw 38; a jaw portion 50 hingedly fastened to the jaw link portion 46 completes the jaw 40.

As stated in the background of the invention, a wide variety of alternatives to the structure described and shown in FIG. 2 are possible. Prominent examples from those incorporated include the structures of U.S. Pat. No. 5,403,312 (Yates et al.) issued Apr. 4, 1995; U.S. Pat. No. 5,395,312 (Desai) issued Mar. 7, 1995; and U.S. Pat. No. 5,318,589 (Lichtman et al.) issued Jun. 7, 1994

Still referring to FIG. 3, a solution supply tube 52 supplies electrolytic solution to an electrode strip 47 along the jaw portion 48, as will be described. A solution supply tube 54 supplies electrolytic solution to a similar strip 49 along the jaw portion 50. A wire 56 electrically connects to the solution supply tube 52; a wire 58 electrically connects to the solution supply tube 54. All the supplies 52, 54, 56, 58, both solution and electrical, extend from the proximal or manual handle end of the shaft 36, and connect to solution and electrical sources.

Figure 4:
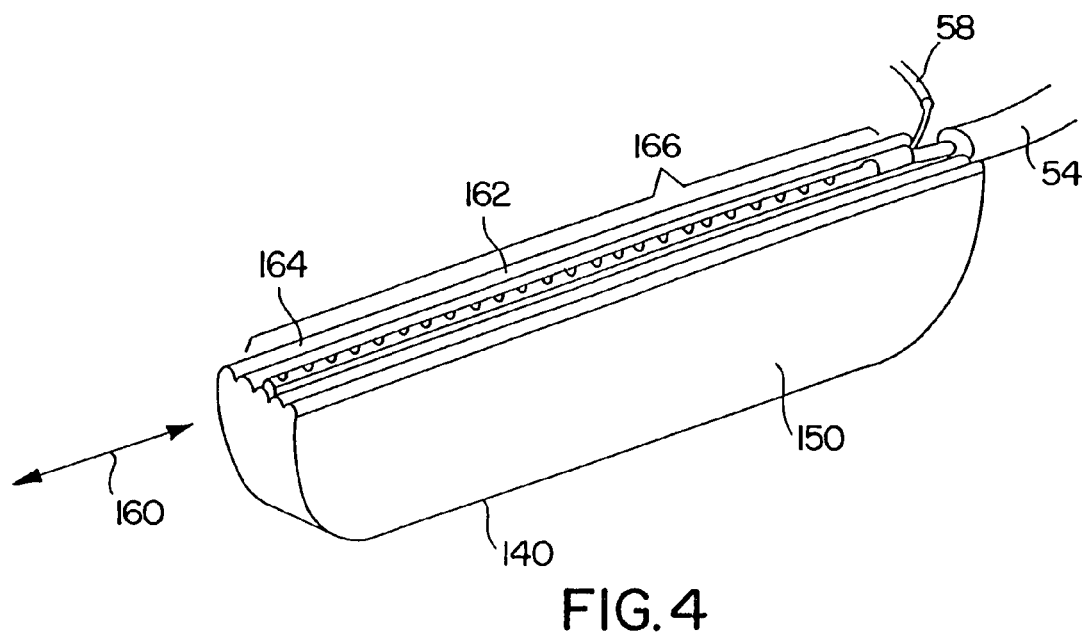
FIG. 4 is a perspective view of a modification of the embodiment of FIG. 2.

Referring to FIG. 4, and in a second form of a jaw, designated 140, a jaw portion 150 similar to jaw portion 50 in FIG. 3, includes a longitudinal dimension in the direction of arrow 160. A plurality of longitudinal grooves 162 are spaced side-by-side across the inner face 164 of the jaw portion 150. The grooves 162 extend the full longitudinal length of the jaw portion 150. The same is true of a mirror image jaw portion, not shown. Both jaw portions are incorporated in a structure as in FIG. 3, and could be placed in substitution for jaw portions 48, 50 in FIG. 3. Grooves, not shown, also preferably extend along the corresponding jaw portions 48, 50 of FIGS. 2-3. Orientations of the grooves other than longitudinal are considered possible, within the limit of construction and arrangement to substantially retain solution along the operative jaw portions.

Bodily tissues to be manipulated have a natural surface roughness. This roughness significantly reduces the area of contact between the forceps jaws and manipulated tissues. Air gaps are created between conventional smooth-surfaced jaws and tissues. If the jaws were energized when dry, electrical resistance in the tissues would be increased, and the current density and tissue temperature would be extremely high. In practice, tissue surfaces are sometimes wet in spots, and yet tissue wetness is not controlled, such that electrical power is to be set on the assumption the inner jaw surfaces are dry. This assumption is necessary to minimize unwanted arcing, charring and smoke.

In contrast, in a forceps according to the invention, whether the jaw portions are grooved or smooth, whether the grooves are longitudinal or otherwise oriented, the jaw portions are uniquely formed of a material such as hollow stainless steel needle tubing such that solution infusion openings 166 may be and are formed in the jaw inner faces such as the inner face 164, as in FIG. 4. Further, the solution supplies 52, 54 shown by example in FIG. 3 may and do open into the openings 166, to supply solution to the openings 166. As most preferred, the openings 166 are laser drilled, and have a diameter in a range centered around four thousandths (0.004) of an inch, and most preferably in a range from two to six thousandths (0.002-0.006) inches.

The purpose of the openings 166 is to infuse solution onto and/or into the tissue adjacent to and otherwise in contact with the forceps jaw portions inner surfaces. It is understood the openings are appropriately as small in diameter as described above to assure more even flow among the openings than would otherwise occur. Further, the openings need not be so closely spaced as to mimic the surface roughness as tissues. Microporous surfaces are possibly acceptable, while they are also not necessary. Infusion of fluid through the jaws is to be maintained in a continuous flow during and throughout the application of RF energy in order for the desired tissue effect to be achieved.

With the described structure and similar structures and methods within the scope of the invention, numerous advantages are obtained. Deeper and quicker coagulation is possible. The conductive solution infused onto and into the tissues maintains relatively consistent maximal electrical contact areas, substantially preventing hot spots and allowing higher power than soft coagulation. Little to no arcing, cutting smoke or char is formed. Jaw and tissue surface temperatures are lower than otherwise, resulting in significantly less adhesion of tissue to jaw surfaces, and substantially no desiccation. One mode of coagulation may be used in the place of the three modes soft, forced, and spray. Coagulation is possible of even the most challenging oozing tissues such as lung, liver and spleen tissues. Coagulation is more precise, where other coagulation modes sometimes spark to the sides and produce coagulation where not desired.

Also, and importantly, electrosurgical cutting by desiccation may be avoided, and tissue sealing achieved. As desired, tissue sealing may occur alone, or be accompanied with mechanical cutting, as by a retractable and advancable blade as in U.S. Pat. No. 5,458,598, and as with blade 1210 in FIG. 12, or otherwise. The tissue sealing itself is understood to occur by flow of electrolytic solution to the manipulating portions of the forceps in combination with energization of the solution with electrical energy, and when included, in combination with pressure on, or compression of, the tissue. Compression of tissue is understood to deform tissues into conditions of sealing of tissues and especially vascalature. Compression of tissue followed by application of solution and energy is understood to permanently maintain compressed deformation of tissue, when present, and to shrink tissue and cause proteins to fix in place. Additional understanding of others is provided in the Yates et al. patent referenced above.

The body of the forceps itself may or not be energized. As most preferred, the solution primarily provides the beneficial functions and effects of the instrument. The effectiveness and extent of the tissue sealing is a function primarily of the type of tissue being manipulated, the quantity of electrolytic solution supplied to the tissue, and the power of the electrical energy supplied to the solution. Tissues not previously considered to be suitable for manipulation, as by cutting, are rendered suitable for manipulation by being sealed against flow of fluids, including bodily fluids and air. With the invention, for example, lung tissue may be cut after sealing, with the tissue adjacent the sealed tissue retaining blood and air. Examples of the principal parameters of specific uses of the invention are provided in the following table. It is understood that the combined consequences of the parameters are that energy density in the tissue to be treated is in a range to effect sealing of the tissue. However, in general, a power output of 7 to 150 watts is preferred.

| Fluid Quantity | Power | Tissue | Effect |
|---|---|---|---|
| 2 cc = s per minute per electrode | 20 watts for 30 seconds | 1 cm diameter vessel | hemostasis through the vessel |
| 2 cc = s per minute per electrode | 30 watts for 45 seconds | lung tissue | hemostasis and aerostasis |
| 4 cc = s per minute per electrode | 40 watts for 90 seconds | 2 cm thickness liver tissue | hemostasis |

In the examples for which the table is provided, the electrolytic solution is saline. In the first example, the device in use was a device as in FIG. 2, with electrodes of 16 gauge tubing, 1 cm long. The tool in use in the second and third examples was a forceps as in FIG. 6, with jaw portions 348, 350, to be described, 4 mm wide and 2.8 cm long. No desiccation was observed at the tissue/electrode interface. The device of FIG. 2 is preferred for vessel closure.

A wide variety of the currently installed electrosurgical generators could be used and will provide proper waveforms and power levels for driving the described forceps. The waveforms need only be sine waves at about 500 kHz, and the power need only be about 30 or more watts. As example of available generators, Valleylab generators are acceptable and widely available.

Figure 8:
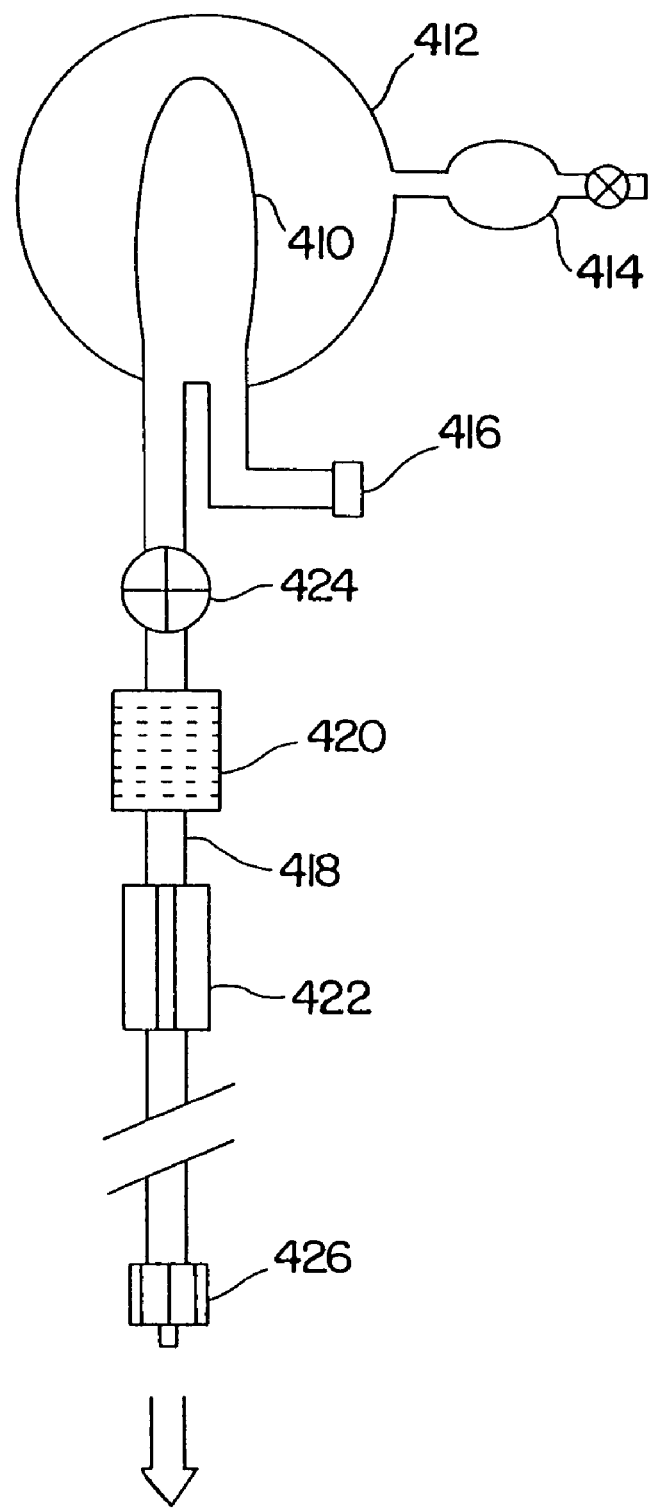
FIG. 8 is a schematic view of preferred saline supply equipment for the invention.

The electrolytic solution supplied to the forceps need only be saline, although a variety of non-toxic and toxic electrolytic solutions are possible. Toxic fluids may be desirable when excising undesired tissues, to prevent seeding during excision. Use of a pressure bulb is possible, as shown in FIG. 8. A flexible reservoir such as an intravenous (IV) bag 410 is surrounded with a more rigid rubber bulb 412 that is pressurized with air through an attached squeeze bulb 414. The reservoir is filled with solution through an injection port 416. An outflow line 418 has a filter 420 and a capillary tube flow restrictor 422 to meter flow. A clamp or valve 424 and connector 426 are also provided. A typical flow rate is one to two (1-2) cc/min at a maximum pressure of approximately sixteen pounds per square inch (16 psi)(52 mmHg). An example of opening diameters, numbers, and flow rate is as follows: opening diameter, 0.16 mm; number of openings, 13 per cm; and flow rate, 2 cc's per minute. A long slit has also been used and found acceptable. In this embodiment, flow rates of 0.01 to 50 cc/min are preferred.

It is understood that highly significant to the invention is the spacing of a plurality of solution openings along the jaw inner surfaces. Single openings as in Ohta et al., that effectively pour fluid adjacent one portion of forceps, are generally not considered suitable or effective. Openings along outer surfaces of the jaws, opposite inner surfaces, are also generally not considered suitable or effective.

Figure 5:
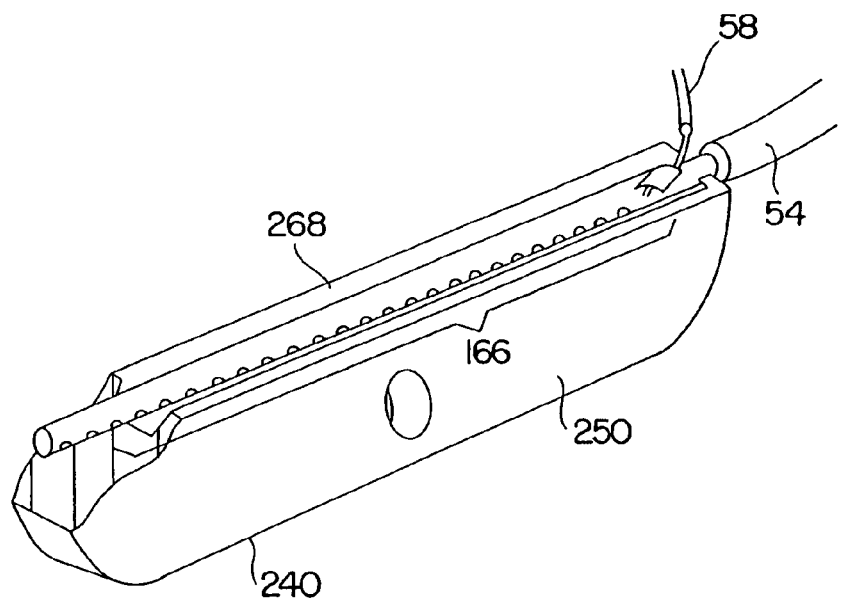
FIG. 5 is a second modification, of the embodiment of FIG. 4, shown partially broken away.

Referring to FIGS. 4 and 5, the configurations of the most preferred solution openings are disclosed. Referring to FIG. 5, in a jaw 240, longitudinally spaced openings 166 are rotated from those shown in FIG. 4, in a jaw portion 250, to turn the openings away from most direct contact with tissues, and more carefully eliminate any unintended plugging of the openings. Electrical insulators 268 in the form of elongated strips extend alongside the tubes which include the openings 166.

Figure 6:
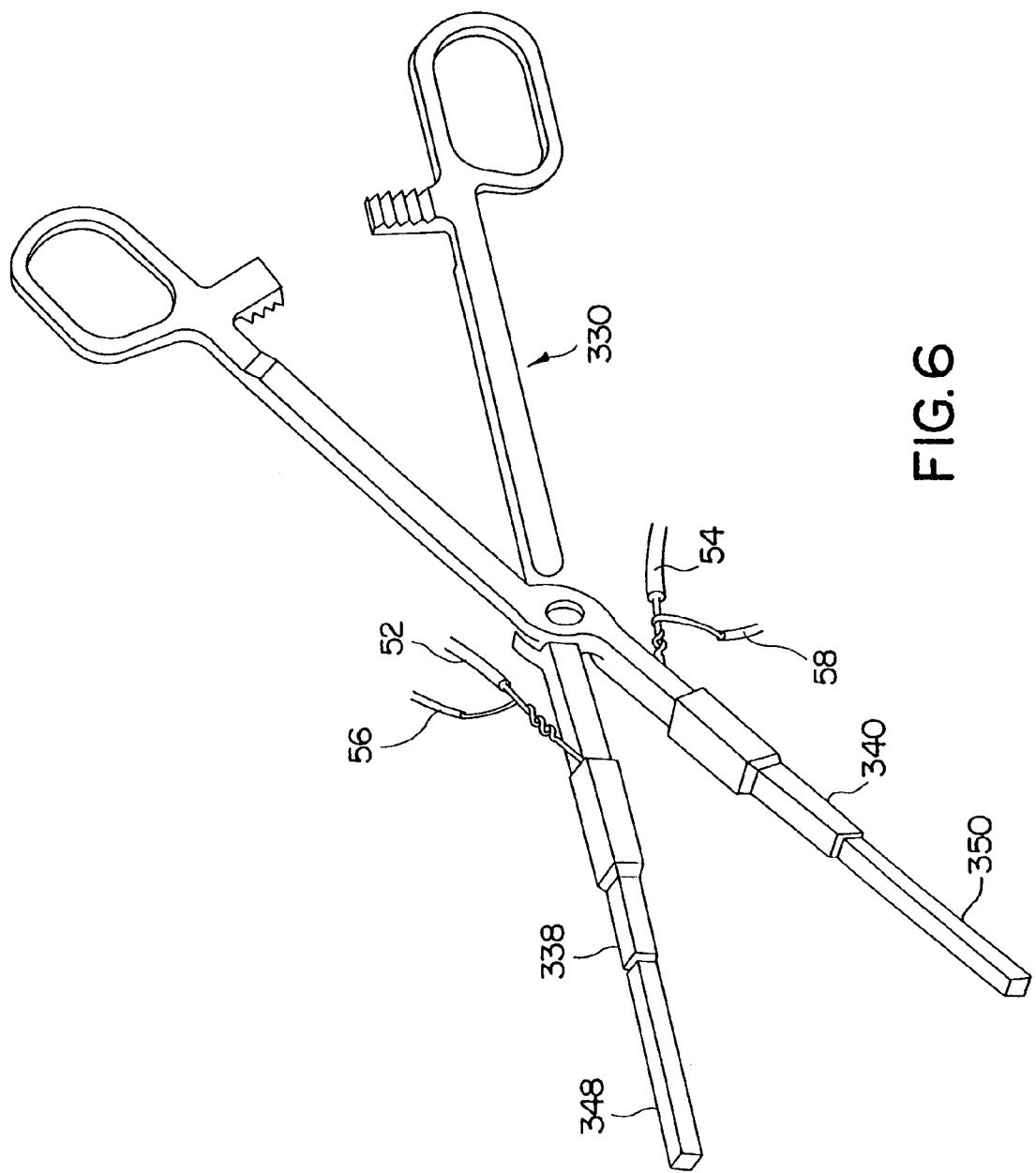
FIG. 6 is a perspective view of an open surgery forceps according to the invention.
Figure 7:
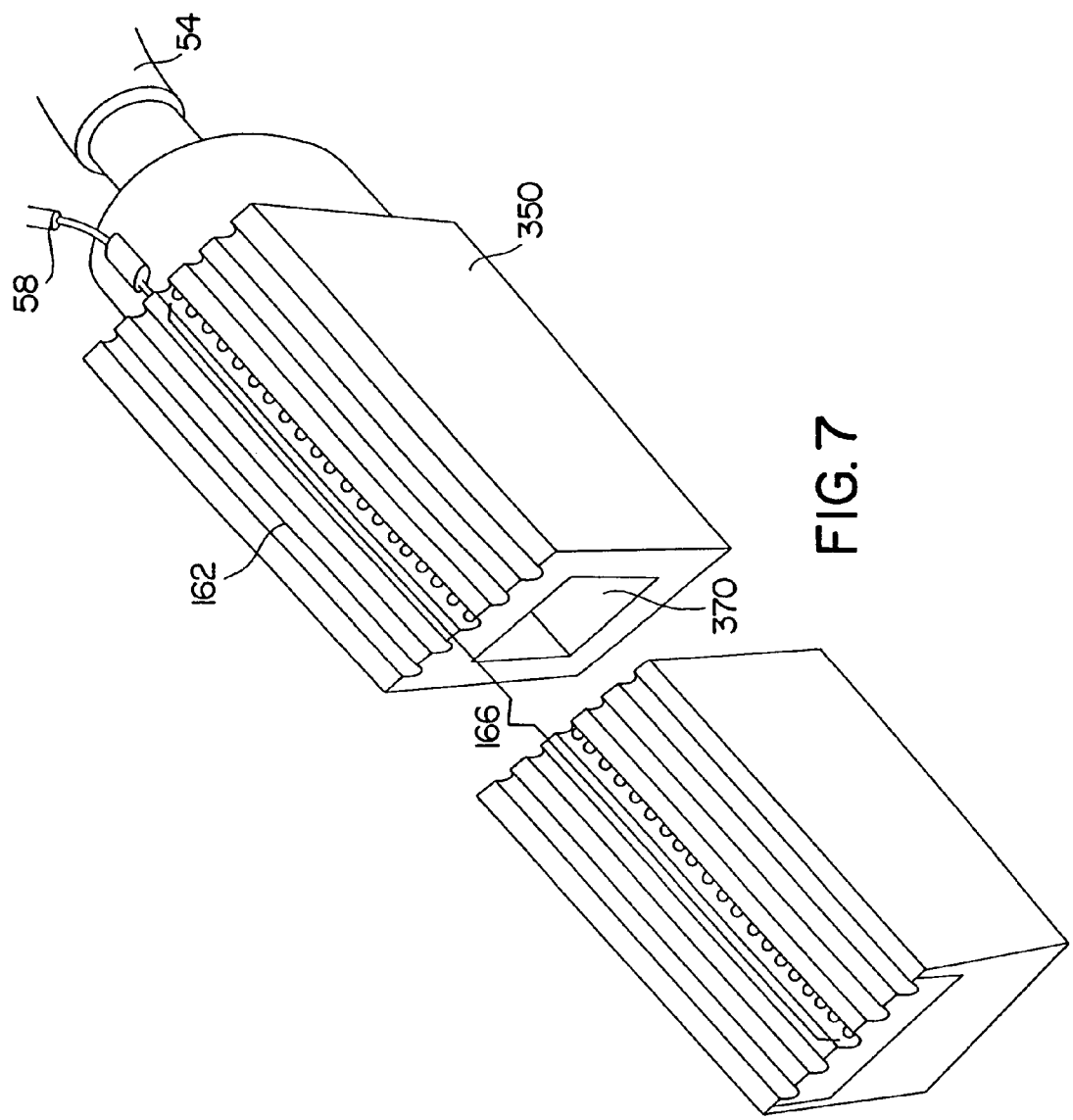
FIG. 7 is a detail view of a portion of the forceps of FIG. 6, partially broken away.

Referring to FIG. 6, open surgical forceps 330 include jaws 338, 340 with jaw portions 348, 350. As with jaw portion 350 in FIG. 7, the jaw portions 348, 350 include spaced solution infusion openings 166 in the central longitudinal groove of a plurality of grooves 162. A central channel 370 of both jaw portions 348, 350, as shown relative to jaw portion 350 in FIG. 7, supplies solution to the openings 166 from solution supplies 52, 54. As with the endoscopic forceps of FIGS. 2-5, the open surgical forceps 330 benefits from the unique enhancement of electrosurgical functions through the infusion of electrolytic solutions onto and into tissues through the spaced, laser drilled, solution infusion openings in the grooves 162.

Figure 9:
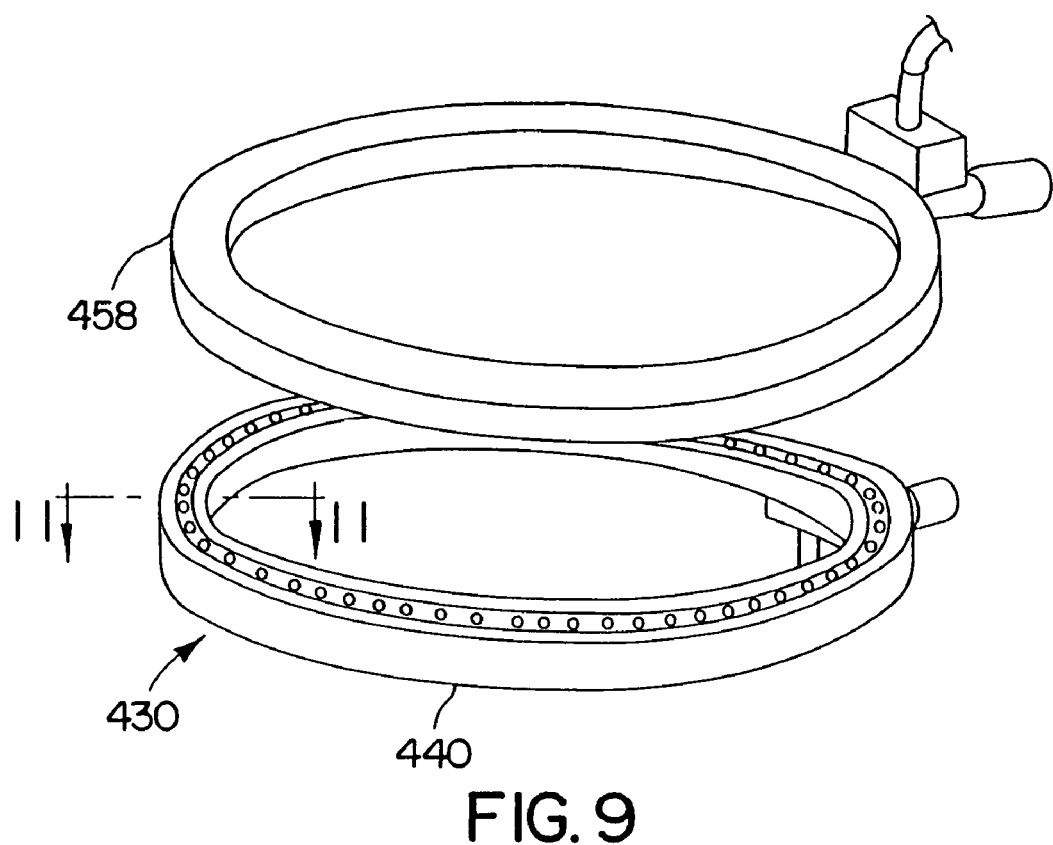
FIG. 9 is a perspective view of a portion of the jaws of an alternative device.
Figure 10:
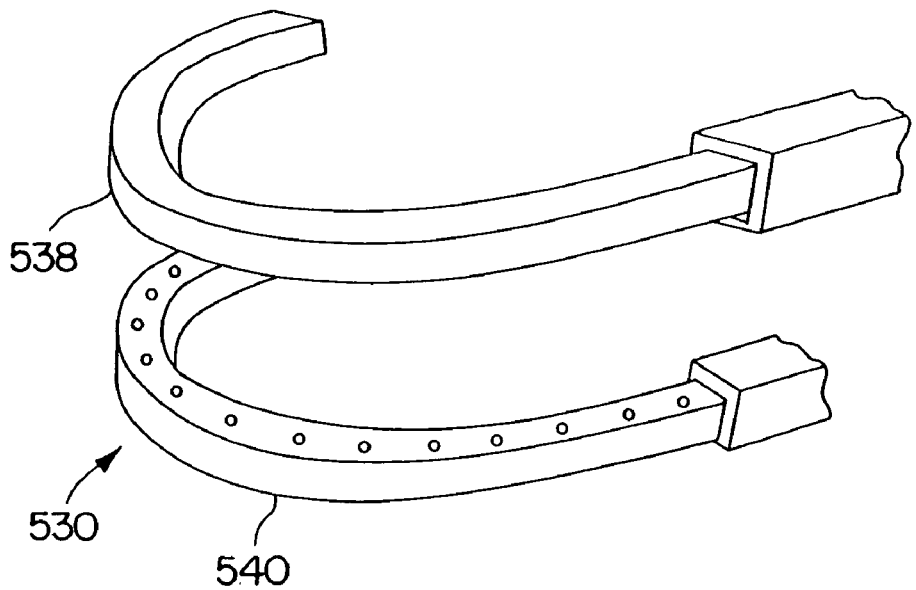
FIG. 10 is a perspective view similar to FIG. 9 of another alternative device.
Figure 11:
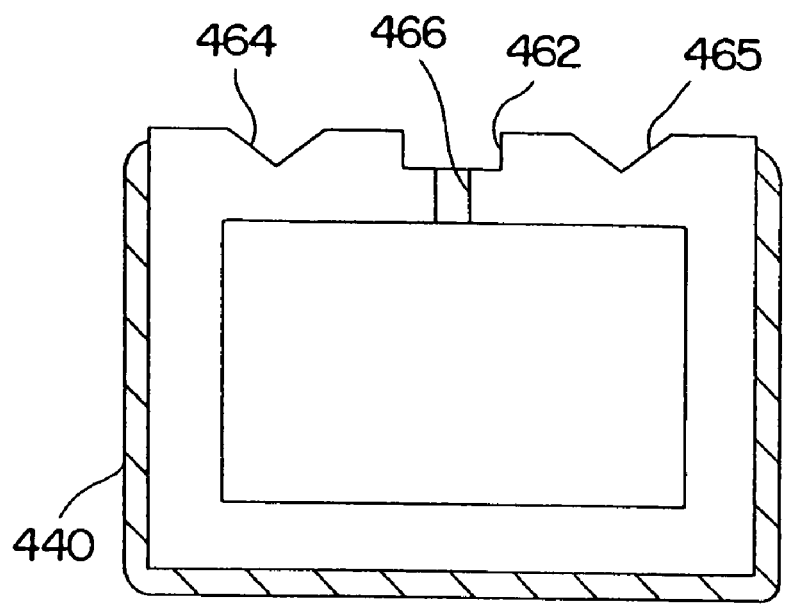
FIG. 11 is a cross-sectional view along line 11-11 of FIG. 9.

Referring to FIGS. 9 and 10, open surgical devices 430 and 530 also include jaws 438, 440 and 538, 540, respectively. The jaw portions of these devices are curved, and in the case of device 430, circular, to adapt the invention to specialized surgical situations of tissue manipulation, such as those in which fluid flow is to be terminated all around a tissue to be isolated and resected or excised. An example of such a tissue is a lesion or tumor of lung tissue. In endoscopic or open surgery, such lesions or tumors may be encircled and/or isolated, surrounding tissue sealed, and the lesions or tumors thereafter resected. Preferably, a one centimeter margin is resected about any lesion or tumor, with the lesion or tumor. As shown, the devices 430, 530 are formed of substantially square cross-section tubing, best shown in the cross-sectional drawing of FIG. 11. As most preferred, the tubing incorporates a central, depressed, cross-sectionally rectangular, and elongated groove 462 and equilaterally spaced, cross-sectionally triangular, parallel, and elongated outer grooves 464, 465. Laser drilled openings 466, similar to openings 166 described above, are located in and spaced along the central groove 462.

Figure 12:
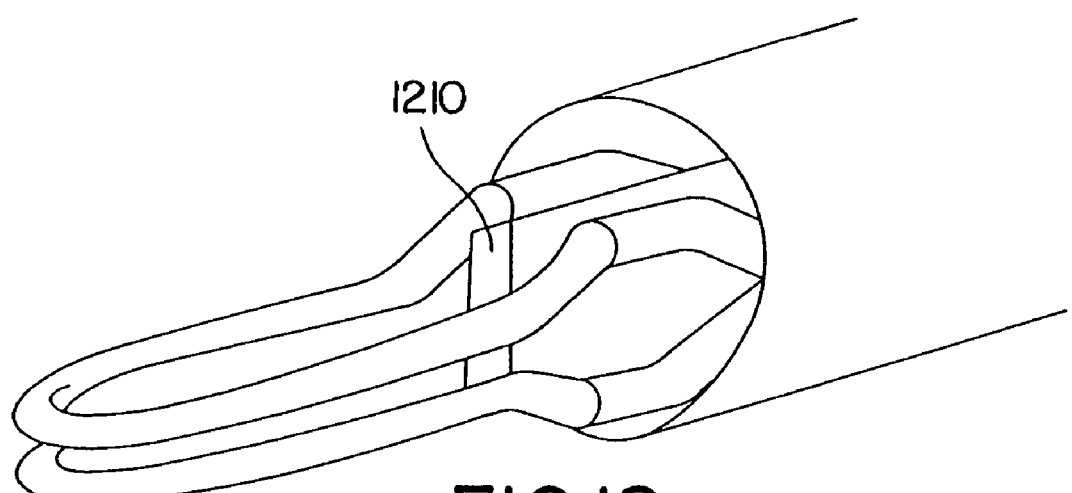
FIG. 12 is a perspective view of yet another alternative device.

Alternate cross-sectional shapes of tubing may be employed, as exemplified in FIG. 12. Flatter operative, e.g., inner faces of tubing are preferred within limits of constructing and arranging the operative faces to facilitate firm grasping and holding of tissue. Non-operative surfaces, being less of concern, may adapt to a variety of contours for a variety of alternate reasons. Further, malleable tubing may be employed, to permit the surgeon to shape the operative portions of the invented devices to specific physiological situations.

The infusion of conductive solutions, referred to here also as electrolytic solutions, simultaneously with the application of RF energy to tissues is discussed in further detail in U.S. Pat. No. 5,431,649 entitled "Method and Apparatus for R-F Ablation," in the name of Peter M. J. Mulier and Michael F. Hoey; in U.S. Pat. No. 5,609,151, entitled "Method and Apparatus for R-F Ablation," in the name of Peter M. J. Mulier. The foregoing patents are commonly assigned to the assignee of the present invention, and are incorporated by reference here.

The preferred embodiments, and the processes of making and using them, are now considered to be described in such full, clear, concise and exact terms as to enable a person of skill in the art to make and use the same. Those skilled in the art will recognize that the preferred embodiments may be altered and modified without departing from the true spirit and scope of the invention as defined in the appended claims. For example, if the invented device is incorporated in forceps, the forceps may be varied in a range from excision and cutting biopsy forceps, to endoscopic forceps, dissecting forceps, and traumatic, atraumatic and flexible endoscopic grasping forceps. The jaws may close into full and tight contact with each other, or close into spaced relationship to each other, to accommodate tissue for purposes other than cutting. As expressed above, parallel spaced relationship is considered most preferably for uniformity of application of pressure across tissue to be affected.

A variety of features such as jaw serrations, single acting and double acting jaws, closing springs, ratchet locks, fingertip rotation rings, color coding and smoke aspiration may or may not be included with the features described in detail. Devices according to the invention may be constructed and arranged to grasp, hold, fix, cut, dissect, expose, remove, extract, retrieve, and otherwise manipulate and treat organs, tissues, tissue masses, and objects. Endoscopic forceps according to the invention may be designed to be used through a trocar. Bipolar and monopolar currents may both be used. With monopolar current, grounding pads may be placed under patients. The described grooves may be eliminated in favor of alternative grooves.

For purposes of the appended claims, the term "manipulate" includes the described functions of grasping, holding, fixing, cutting, dissecting, exposing, removing, extracting, retrieving, coagulating, ablating and otherwise manipulating or similarly treating organs, tissues, tissue masses, and objects. Also for purposes of the appended claims, the term "tissue" includes organs, tissues, tissue masses, and objects. Further for purposes of the appended claims, the term "electrical energy sufficient to affect tissue" includes electrical energy sufficient to raise tissue temperature to cause non-reversible effect on tissue as described above.

To particularly point out and distinctly claim the subject matter regarded as invention, the following claims conclude this specification.

We claim:

1. A method of isolating an area of tissue from surrounding tissue of a patient comprising:
providing a device comprising a device jaw having a first jaw arm including a first ablation element and a second jaw arm including a second ablation element, the device further comprising at least one solution infusion opening defined along each of the first and second jaw arms;
placing tissue surrounding the area of tissue to be isolated within the device jaw;
supplying RF energy from an RF energy source to the first and second ablation elements; and
ablating the tissue placed within the device jaw to at least partially isolate the area of tissue.

2. The method of claim 1 further comprising supplying an electrolytic solution to the at least one solution infusion opening of each of the first and second jaw arms.

3. The method of claim 2 wherein the electrolytic solution is supplied at a rate in a range of about 0.01 to about 100 cc/mm.

4. The method of claim 2 wherein the electrolytic solution is supplied from a reservoir.

5. The method of claim 4 wherein the reservoir is an IV bag.

6. The method of claim 4 wherein the electrolytic solution is a saline solution.

7. The method of claim 1 wherein at least a portion of each of the first and second jaw arms is linear.

8. The method of claim 1 wherein each of the first and second jaw arms includes a porous surface.

9. The method of claim 1 wherein at least a portion of each of the first and second jaw arms is malleable.

10. The method of claim 1 wherein the device further comprises a shaft extending from the first and second jaw arms, the shaft and jaws arms being sized to permit endoscopic use of the device.

11. The method of claim 1 wherein the first and second jaw arms are sized for passing through a trocar.

12. The method of claim 1 wherein the first and second jaw arms are capable of being moved in a parallel spaced relationship.

13. The method of claim 1 wherein the device further comprises a pivot for pivoting movement of the first and second jaw arms towards each other and away from each other.

14. The method of claim 1 wherein the first and second ablation elements each comprise an elongated insulator extending along the jaw arm and an elongated electrode in a partially recessed portion with respect to the elongated insulator.

15. The method of claim 1 wherein at least a portion of the first ablation element is on an inner face of the first jaw arm and at least a portion of the second ablation element is on an inner face of the second jaw arm, the first and second ablation elements each comprise an elongated electrode.

16. A method of isolating an area of tissue from surrounding tissue of a patient comprising:
providing a device comprising a device jaw having a first jaw arm including a first ablation element and a second jaw arm including a second ablation element, wherein each of the first and second jaw arms includes a porous surface;
placing tissue surrounding the area of tissue to be isolated within the device jaw;
supplying RF energy from an RF energy source to the first and second ablation elements; and
ablating the tissue placed within the device jaw to at least partially isolate the area of tissue.

17. The method of claim 16 wherein the first and second jaw arms are sized for passing through a trocar.

18. The method of claim 16 wherein the first and second jaw arms each have a portion on an inner face for engaging tissue.

19. The method of claim 16 wherein the device further comprises a handle and a mechanism connected to the handle and to the first and second jaw arms, whereby the movement of the first jaw arm in relationship to the second jaw arm may be manipulated from the handle.

20. The method of claim 16 wherein the first and second jaw arms each have a curved portion corresponding to the contour of the tissue to be ablated.

21. The method of claim 16 wherein at least a portion of each of the first and second jaw arms is linear.

22. The method of claim 16 wherein at least a portion of each of the first and second jaw arms is malleable.

23. The method of claim 16 wherein the device further comprises a shaft extending from the first and second jaw arms, the shaft and jaws arms being sized to permit endoscopic use of the device.

24. The method of claim 16 wherein the first and second jaw arms are capable of being moved in a parallel spaced relationship.

25. The method of claim 16 wherein the device further comprises a pivot for pivoting movement of the first and second jaw arms towards each other and away from each other.

26. The method of claim 16 wherein the first and second ablation elements each comprise an elongated insulator extending along the jaw arm and an elongated electrode in a partially recessed portion with respect to the elongated insulator.

27. The method of claim 16 wherein at least a portion of the first ablation element is on an inner face of the first jaw arm and at least a portion of the second ablation element is on an inner face of the second jaw arm, the first and second ablation elements each comprise an elongated electrode.

28. The method of claim 16 wherein the device further comprises at least one solution infusion opening defined along each of the first and second jaw arms.

29. The method of claim 28 further comprising supplying an electrolytic solution to the at least one solution infusion opening of each of the first and second jaw arms.

30. A method of isolating an area of tissue from surrounding tissue of a patient comprising:
providing a device comprising a device jaw having a first jaw arm including a first ablation element and a second jaw arm including a second ablation element, wherein the device further comprises a pivot for pivoting movement of the first and second jaw arms towards each other and away from each other;
placing tissue surrounding the area of tissue to be isolated within the device jaw;
supplying RF energy from an RF energy source to the first and second ablation elements;
ablating the tissue placed within the device jaw to at least partially isolate the area of tissue; and wherein first and second jaw arms each have a surface comprising an elongated insulator extending along the jaw arm and an elongated electrode in a partially recessed position with respect to the elongated insulator, the elongated electrode of the first jaw arm aligned in a substantially parallel spaced relationship with the elongated electrode of the second jaw arm when the jaw arms are in a position for ablating tissue placed within the device jaws.

31. The method of claim 30 wherein the first and second jaw arms are capable of being moved relative to each other in a parallel spaced relationship.

32. The method of claim 30 wherein the RF energy source is a RF generator.

33. The method of claim 32 wherein the RF generator provides RF energy having a sine wave waveform.

34. The method of claim 33 wherein the sine wave waveform has a frequency of about 500 kHz.

35. The method of claim 30 wherein the RF energy is supplied at a power in a range of about 1 to about 200 watts.

36. The method of claim 30 wherein the device further comprises a mechanism configured to substantially uniformly apply pressure to tissue placed within the device jaws.

37. The method of claim 30 wherein each of the first and second jaw arms includes a porous surface.

38. A method of isolating an area of tissue from surrounding tissue of a patient comprising:
providing a device comprising a device jaw having a first jaw arm including a first ablation element and a second jaw arm including a second ablation element, wherein the first jaw arm includes a first ablative portion on an inner face and the second jaw arm includes a second ablative portion on an inner face, the first and second ablative portions of the first and second jaw arms configured in at least one convex portion for engaging tissue between the first and second jaw arms;
placing tissue surrounding the area of tissue to be isolated within the device jaw;
supplying RF energy from an RF energy source to the first and second ablation elements;
ablating the tissue placed within the device jaw to at least partially isolate the area of tissue; and
wherein the first and second ablative portions each comprise an elongated insulator extending along the jaw arm and an elongated electrode in a partially recessed position with respect to the elongated insulator.

39. A method of ablating tissue of a patient comprising:
placing tissue between a first jaw arm and a second jaw arm of a device, the first and second jaws including opposed jaw portions on inner faces thereof for engaging tissue, each of the inner faces comprising an insulating portion and an ablative portion with the ablative portion being centrally located with respect to the insulating portion, the inner faces arranged on the jaws such that the inner faces are adapted to grasp tissue placed between them, the device further comprising at least one solution infusion opening defined along each of the first and second jaw arms;
moving the first jaw and the second jaw into engagement with the tissue placed between them such that the inner faces are substantially parallel as the tissue is grasped between them; and
supplying RF energy from an RF energy source to the ablative portions of the first and second jaws to ablate the tissue grasped between the first and second jaws.

40. The method of claim 39 wherein each of the first and second jaw arms is malleable.

41. The method of claim 39 further comprising supplying an electrolytic solution to the at least one solution infusion opening of each of the first and second jaw arms.

42. The method of claim 41 wherein the electrolytic solution is supplied from a reservoir.

43. The method of claim 42 wherein the reservoir is an IV bag.

44. The method of claim 43 wherein the electrolytic solution is a saline solution.

45. The method of claim 41 wherein the electrolytic solution is supplied at a rate in a range of about 0.01 to about 100 cc/mm.

46. A method of ablating tissue of a patient comprising:
placing tissue between a first jaw arm and a second jaw arm of a device, wherein each of the first and second jaw arms includes a porous surface, the first and second jaws including opposed jaw portions on inner faces thereof for engaging tissue, each of the inner faces comprising an insulating portion and an ablative portion with the ablative portion being centrally located with respect to the insulating portion, the inner faces arranged on the jaws such that the inner faces are adapted to grasp tissue placed between them;
moving the first jaw and the second jaw into engagement with the tissue placed between them such that the inner faces are substantially parallel as the tissue is grasped between them; and
supplying RF energy from an RF energy source to the ablative portions of the first and second jaws to ablate the tissue grasped between the first and second jaws.

47. The method of claim 46 wherein the first and second jaw arms are sized for passing through a trocar.

48. A method of ablating tissue of a patient comprising:
placing tissue between a first jaw arm and a second jaw arm of a device, wherein at least a portion of the first and second jaw arms is curved, the first and second jaws including opposed jaw portions on inner faces thereof for engaging tissue, each of the inner faces comprising an insulating portion and an ablative portion with the ablative portion being centrally located with respect to the insulating portion, the inner faces arranged on the jaws such that the inner faces are adapted to grasp tissue placed between them;
moving the first jaw and the second jaw into engagement with the tissue placed between them such that the inner faces are substantially parallel as the tissue is grasped between them; and
supplying RF energy from an RF energy source to the ablative portions of the first and second jaws to ablate the tissue grasped between the first and second jaws; and
wherein the first and second jaw arms each have a curved portion corresponding to the contour of the tissue to be ablated.

49. The method of claim 48 wherein at least a portion of the first and second jaw arms is linear.

50. A method of ablating tissue of a patient comprising:
placing tissue between a first jaw arm and a second jaw arm of a device, wherein at least a portion of the first and second jaw arms is curved, the first and second jaws including opposed jaw portions on inner faces thereof for engaging tissue, each of the inner faces comprising an insulating portion and an ablative portion with the ablative portion being centrally located with respect to the insulating portion, the inner faces arranged on the jaws such that the inner faces are adapted to grasp tissue placed between them;

moving the first jaw and the second jaw into engagement with the tissue placed between them such that the inner faces are substantially parallel as the tissue is grasped between them; and supplying RF energy from an RF energy source to the ablative portions of the first and second jaws to ablate the tissue grasped between the first and second jaws; and wherein the device further comprises a handle and a mechanism connected to the handle and to the first and second jaw arms, whereby the movement of the first jaw arm in relationship to the second jaw arm may be manipulated from the handle.

51. The method of claim 50 wherein at least a portion of the first and second jaw arms is malleable.

52. A method of ablating tissue comprising:
selecting a device comprising a device jaw having a first malleable jaw arm and a second malleable jaw arm, the first jaw arm includes an ablative portion, the device further comprising at least one solution infusion opening defined along the first jaw arm;
shaping the first and second jaw arms to a specific physiological situation;
placing tissue within the device jaw;
moving the first jaw arm and the second jaw arm into engagement with the tissue placed within the device jaw such that the first and second jaw arms are substantially parallel as the tissue within the device jaw is engaged;
supplying RF energy from an RF energy source to the ablative portion; and
ablating the tissue placed within the device jaw.

53. The method of claim 52 wherein at least a portion of each of the first and second jaw arms is linear.

54. The method of claim 52 further comprising supplying an electrolytic solution to the at least one solution infusion opening of the first jaw arm.

55. The method of claim 54 wherein the electrolytic solution is supplied from a reservoir.

56. The method of claim 55 wherein the reservoir is an IV bag.

57. The method of claim 55 wherein the electrolytic solution is a saline solution.

58. The method of claim 55 wherein the electrolytic solution is supplied at a rate in a range of about 0.01 to about 100 cc/mm.

59. A method of ablating tissue comprising:
selecting a device comprising a device jaw having a first malleable jaw arm and a second malleable jaw arm, wherein the first jaw arm includes a porous surface and an ablative portion;
shaping the first and second jaw arms to a specific physiological situation;
placing tissue within the device jaw;
moving the first jaw arm and the second jaw arm into engagement with the tissue placed within the device jaw such that the first and second jaw arms are substantially parallel as the tissue within the device jaw is engaged;
supplying RF energy from an RF energy source to the ablative portion; and
ablating the tissue placed within the device jaw.

60. The method of claim 59 wherein the first and second jaw arms are sized for passing through a trocar.

61. A method of isolating an area of tissue from surrounding tissue of a patient comprising:
providing a device comprising a device jaw having a first jaw arm including a first ablation element and a second jaw arm including a second ablation element, wherein at least a portion of each of the first and second jaw arms is curved;
placing tissue surrounding the area of tissue to be isolated within the device jaw;
supplying RF energy from an RF energy source to the first and second ablation elements; and
ablating the tissue placed within the device jaw to at least partially isolate the area of tissue, wherein each of the first and second jaw arms includes a porous surface.

62. A method of isolating an area of tissue from surrounding tissue of a patient comprising:
providing a device comprising a device jaw having a first jaw arm including a first ablation element and a second jaw arm including a second ablation element, wherein at least a portion of each of the first and second jaw arms is curved;
placing tissue surrounding the area of tissue to be isolated within the device jaw;
supplying RF energy from an RF energy source to the first and second ablation elements; and
ablating the tissue placed within the device jaw to at least partially isolate the area of tissue, wherein the device further comprises at least one solution infusion opening defined along each of the first and second jaw arms.

63. The method of claim 62 further comprising supplying an electrolytic solution to the at least one solution infusion opening of each of the first and second jaw arms.

64. A method of isolating an area of tissue from surrounding tissue of a patient comprising:
providing a device comprising a device jaw having a first jaw arm including a first ablation element and a second jaw arm including a second ablation element, wherein at least a portion of each of the first and second jaw arms is curved;
placing tissue surrounding the area of tissue to be isolated within the device jaw;
supplying RF energy from an RF energy source to the first and second ablation elements; and
ablating the tissue placed within the device jaw to at least partially isolate the area of tissue, wherein the first and second ablation elements each comprise an elongated insulator extending along the jaw arm and an elongated electrode in a partially recessed portion with respect to the elongated insulator.

65. The method of claim 64 wherein at least a portion of the first ablation element is on an inner face of the first jaw arm and at least a portion of the second ablation element is on an inner face of the second jaw arm.

66. The method of claim 64 wherein at least a portion of each of the first and second jaw arms is linear.

67. The method of claim 64 wherein at least a portion of each of the first and second jaw arms is malleable.

68. The method of claim 64 wherein the first and second jaw arms are sized for passing through a trocar.

69. The method of claim 64 wherein the first and second jaw arms are capable of being moved in a parallel spaced relationship.

70. A method of isolating an area of tissue from surrounding tissue of a patient comprising:
providing a device comprising a device jaw having a first jaw arm including a first ablation element and a second jaw arm including a second ablation element, wherein the device further comprises a handle and a mechanism connected to the handle and to the first and second jaw arms, whereby the movement of the first jaw arm in relationship to the second jaw arm may be manipulated from the handle, wherein the device further comprises a shaft extending from the handle to the first and second jaw arms, the shaft and jaws arms being sized to permit endoscopic use of the device;

placing tissue surrounding the area of tissue to be isolated within the device jaw;

supplying RF energy from an RF energy source to the first and second ablation elements; and ablating the tissue placed within the device jaw to at least partially isolate the area of tissue, wherein the first and second ablation elements each comprise an elongated insulator extending along the jaw arm and an elongated electrode in a partially recessed portion with respect to the elongated insulator.

71. The method of claim 70 wherein at least a portion of the first ablation element is on an inner face of the first jaw arm and at least a portion of the second ablation element is on an inner face of the second jaw arm.

72. A method of isolating an area of tissue from surrounding tissue of a patient comprising:

providing a device comprising a device jaw having a first jaw arm including a first ablation element and a second jaw arm including a second ablation element, wherein the device further comprises a handle and a mechanism connected to the handle and to the first and second jaw arms, whereby the movement of the first jaw arm in relationship to the second jaw arm may be manipulated from the handle, wherein the device further comprises a shaft extending from the handle to the first and second jaw arms, the shaft and jaws arms being sized to permit endoscopic use of the device;

placing tissue surrounding the area of tissue to be isolated within the device jaw;

supplying RF energy from an RF energy source to the first and second ablation elements; and ablating the tissue placed within the device jaw to at least partially isolate the area of tissue, wherein the device further comprises at least one solution infusion opening defined along each of the first and second jaw arms.

73. The method of claim 72 further comprising supplying an electrolytic solution to the at least one solution infusion opening of each of the first and second jaw arms.

74. A method of isolating an area of tissue from surrounding tissue of a patient comprising:

providing a device comprising a device jaw having a first jaw arm including a first ablation element and a second jaw arm including a second ablation element, wherein the device further comprises a handle and a mechanism connected to the handle and to the first and second jaw arms, whereby the movement of the first jaw arm in relationship to the second jaw arm may be manipulated from the handle, wherein the device further comprises a shaft extending from the handle to the first and second jaw arms, the shaft and jaws arms being sized to permit endoscopic use of the device;

placing tissue surrounding the area of tissue to be isolated within the device jaw;

supplying RF energy from an RF energy source to the first and second ablation elements; and ablating the tissue placed within the device jaw to at least partially isolate the area of tissue, wherein each of the first and second jaw arms includes a porous surface.

75. A method of isolating an area of tissue from surrounding tissue of a patient comprising:

providing a device comprising a device jaw having a first jaw arm including a first ablation element and a second jaw arm including a second ablation element, wherein the device further comprises a pivot for pivoting movement of the first and second jaw arms towards each other and away from each other;

placing tissue surrounding the area of tissue to be isolated within the device jaw;

supplying RF energy from an RF energy source to the first and second ablation elements;

ablating the tissue placed within the device jaw to at least partially isolate the area of tissue; and wherein the device further comprises a shaft extending from the first and second jaw arms, the shaft and jaws arms being sized to permit endoscopic use of the device.

76. The method of claim 75 wherein at least a portion of each of the first and second jaw arms is linear.

77. The method of claim 75 wherein at least a portion of each of the first and second jaw arms is malleable.

78. The method of claim 75 wherein the first and second jaw arms are sized for passing through a trocar.

79. A method of isolating an area of tissue from surrounding tissue of a patient comprising:

providing a device comprising a device jaw having a first jaw arm including a first ablation element and a second jaw arm including a second ablation element, wherein the device further comprises a pivot for pivoting movement of the first and second jaw arms towards each other and away from each other;

placing tissue surrounding the area of tissue to be isolated within the device jaw;

supplying RF energy from an RF energy source to the first and second ablation elements; and wherein the first and second ablation elements each comprise an elongated insulator extending along the jaw arm and an elongated electrode in a partially recessed portion with respect to the elongated insulator.

80. A method of isolating an area of tissue from surrounding tissue of a patient comprising:

providing a device comprising a device jaw having a first jaw arm including a first ablation element and a second jaw arm including a second ablation element, wherein the device further comprises a pivot for pivoting movement of the first and second jaw arms towards each other and away from each other;

placing tissue surrounding the area of tissue to be isolated within the device jaw;

supplying RF energy from an RF energy source to the first and second ablation elements; and wherein the device further comprises at least one solution infusion opening defined along each of the first and second jaw arms.

81. The method of claim 80 further comprising supplying an electrolytic solution to the at least one solution infusion opening of each of the first and second jaw arms.

82. A method of isolating an area of tissue from surrounding tissue of a patient comprising:

providing a device comprising a device jaw having a first jaw arm including a first ablation element and a second jaw arm including a second ablation element, wherein the first jaw arm includes a first ablative portion on an inner face and the second jaw arm includes a second ablative portion on an inner face, the first and second ablative portions of the first and second jaw arms configured in at least one convex portion for engaging tissue between the first and second jaw arms;

placing tissue surrounding the area of tissue to be isolated within the device jaw;

supplying RF energy from an RF energy source to the first and second ablation elements; ablating the tissue placed within the device jaw to at least partially isolate the area of tissue; and wherein the device further comprises a shaft extending from the first and second jaw arms, the shaft and jaws arms being sized to permit endoscopic use of the device.

83. The method of claim 82 wherein at least a portion of each of the first and second jaw arms is curved.

84. The method of claim 82 wherein the first and second jaw arms each have a curved portion corresponding to the contour of the tissue to be ablated.

85. A method of isolating an area of tissue from surrounding tissue of a patient comprising:

providing a device comprising a device jaw having a first jaw arm including a first ablation element and a second jaw arm including a second ablation element, wherein the first jaw arm includes a first ablative portion on an inner face and the second jaw arm includes a second ablative portion on an inner face, the first and second ablative portions of the first and second jaw arms configured in at least one convex portion for engaging tissue between the first and second jaw arms;

placing tissue surrounding the area of tissue to be isolated within the device jaw;

supplying RF energy from an RF energy source to the first and second ablation elements; ablating the tissue placed within the device jaw to at least partially isolate the area of tissue; and wherein the first and second ablation elements each comprise an elongated insulator extending along the jaw arm and an elongated electrode in a partially recessed portion with respect to the elongated insulator.

86. The method of claim 85 wherein the first and second jaw arms are capable of being moved in a parallel spaced relationship.

87. The method of claim 85 wherein the device further comprises a pivot for pivoting movement of the first and second jaw arms towards each other and away from each other.

88. The method of claim 85 wherein the device further comprises at least one solution infusion opening defined along each of the first and second jaw arms.

89. The method of claim 85 further comprising supplying an electrolytic solution to the at least one solution infusion opening of each of the first and second jaw arms.

90. The method of claim 85 wherein each of the first and second jaw arms includes a porous surface.

* * * * *